(12) United States Patent
Khosla et al.

US007605150B2

(10) Patent No.: US 7,605,150 B2
(45) Date of Patent: Oct. 20, 2009

(54) DRUG THERAPY FOR CELIAC SPRUE

(75) Inventors: Chaitan Khosla, Palo Alto, CA (US);
Felix Hausch, Langenselbold (DE)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 573 days.

(21) Appl. No.: 10/514,177

(22) PCT Filed: May 14, 2003

(86) PCT No.: PCT/US03/15343

§ 371 (c)(1),
(2), (4) Date: Jun. 28, 2005

(87) PCT Pub. No.: WO03/096979

PCT Pub. Date: Nov. 27, 2003

(65) Prior Publication Data
US 2006/0035838 A1 Feb. 16, 2006

Related U.S. Application Data

(60) Provisional application No. 60/380,761, filed on May 14, 2002, provisional application No. 60/392,782, filed on Jun. 28, 2002, provisional application No. 60/422,933, filed on Oct. 31, 2002, provisional application No. 60/428,033, filed on Nov. 20, 2002.

(51) Int. Cl.
*A61K 31/60* (2006.01)
*A61K 38/00* (2006.01)
*A51K 38/04* (2006.01)
*A01N 31/00* (2006.01)

(52) U.S. Cl. ........................ 514/160; 530/324; 530/325; 530/326; 530/327; 530/328; 530/329; 514/2; 424/1.69

(58) Field of Classification Search .................. 514/160
See application file for complete search history.

(56) References Cited

U.S. PATENT DOCUMENTS

| | | | |
|---|---|---|---|
| 4,203,967 A | 5/1980 | Gallo-Torres | |
| 4,912,120 A | 3/1990 | Castelhano et al. | |
| 4,929,630 A | 5/1990 | Castelhano et al. | |
| 5,372,933 A * | 12/1994 | Zamarron et al. | 435/7.21 |
| 5,817,523 A | 10/1998 | Picarelli | |
| 5,834,428 A | 11/1998 | Drucker | |
| 6,197,356 B1 | 3/2001 | Girsh | |
| 6,319,726 B1 | 11/2001 | Schuppan et al. | |
| 6,410,550 B1 | 6/2002 | Coe et al. | |
| 2001/0007690 A1 | 7/2001 | Girsh | |
| 2001/0036639 A1 | 11/2001 | Fine | |
| 2002/0039599 A1 | 4/2002 | Lin et al. | |
| 2002/0076834 A1 | 6/2002 | Detlef et al. | |
| 2003/0215438 A1 | 11/2003 | Hausch et al. | |
| 2003/0224476 A1 | 12/2003 | Chou | |
| 2004/0167069 A1 | 8/2004 | Khosla et al. | |
| 2004/0241664 A1 | 12/2004 | Dekker et al. | |
| 2005/0090653 A1 | 4/2005 | Klaveness et al. | |

FOREIGN PATENT DOCUMENTS

| | | |
|---|---|---|
| EP | 0237082 | 9/1987 |
| EP | 0 905 518 A1 | 3/1999 |
| WO | WO 94/26774 | 11/1994 |
| WO | 0125793 | 4/2001 |
| WO | WO 03/068170 | 8/2003 |

OTHER PUBLICATIONS

Freund, K., et al., "Transglutaminase inhibition by 2-[(2-Oxopropyl)thio]imidazolium derivatives: mechanism of factor XIIIa inactivation," 1994 *Biochemistry*, 33:10109-10119.

Ahnen et al., "Intestinal aminooligopeptidase. In vivo synthesis on intracellular membranes of rat jejunum" J. Biol. Chem., 1982, pp. 12129-12135, vol. 257.

Arentz-Hansen et al. "Celiac Lesion T Cells Recognizes Epitopes that Cluster in Regions of Gliadins Rich in Proline Residues" Gastroenterology, 2002, pp. 803-809, vol. 123, No. 3.

Arentz-Hansen et al., "The Intestinal T Cell Response To a—Gliadin In Adult Celiac Disease Is Focused On A Single Deamidated Glutamine Targeted By Tissue Transglutaminase" J. Exp. Med., 2000, pp. 603-612, vol. 191.

Bordusa et al., "The Specificity Of Prolyl Endopeptidase From *Flavobacterium meningoseptum*: Mapping the S' Subsites By Positional Scanning Via Acyl Transfer" Bioorg. Med. Chem., 1998, pp. 1775-1780, vol. 6.

Castelhano et al., "Synthesis, Chemistry, and Absolute Configuratin of Novel Transglutaminiase Inhibitors Containing a 3-Halo-4,5-dihydroisoxazole" Bioorg. Chem., 1988, pp. 335-340, vol. 16.

Choi et al. "Chemistry and Biology of Dihydroisoxazole Derivatives: Selectives Inhibitors of Human Transglutaminase 2" Chem. & Biol., 2005, pp. 469-475, vol. 12.

Colot et al. "The Genes Encoding Wheat Storage Proteins: Towards A Molecular Understanding Of Bread-Making Quality And Its Genetic Manipulation" Genet Eng, 1990, pp. 225-241, vol. 12.

Database Derwent, Acc-No. 1996-329479, JP-08151396A, HLA-binding oligopeptide and an immuno: regulator contg, it-used in the treatment of auto: immune diseases, Abstract, Jun. 11, 1996.

de Ritis G. et al. "In Vitro (organ culture) Studies of the Toxicity of Specific A-Gliadin Peptides in celiac Disease" Gastroenbterology, 1988, pp. 41-49, vol. 94.

Frazer et al. "Gluten-induced enteropathy: the effect of partially digested gluten." Lancet, Sep. 5, 1959, pp. 252-255, vol. 2.

Greenberg, C. et al. "Transglutaminases: multifunctional cross-linking enzymes that stabilize tissues" FASEB J., 1991, pp. 3071-3077, vol. 5.

(Continued)

*Primary Examiner*—Cecilia Tsang
*Assistant Examiner*—Maury Audet
(74) *Attorney, Agent, or Firm*—Bozicevic, Field & Francis LLP; Pamela J. Sherwood

(57) ABSTRACT

Administering an effective dose of a tTGase inhibitor to a Celiac or dermatitis herpetiformis patient reduces the toxic effects of toxic gluten oligopeptides, thereby attenuating or eliminating the damaging effects of gluten.

5 Claims, No Drawings

OTHER PUBLICATIONS

Hausch et al. "Design, synthesis, and evaluation of gluten peptide analogs as selective inhibitors of human tissue transglutaminase" Chem Biol., Mar. 2003, pp. 225-231, vol. 10, Issue 3.

Hitomi, K. et al. "GTP, an inhibitor of transglutaminases, is hydrolyzed by tissue-type transglutaminase (TGase 2) but not by epidermal-type transglutaminase (TGase 3)," Biosci. Biotechnol. Biochem., 2000, pp. 657-659, vol. 64, Issue 3.

Kao Castle Pty Ltd Sequence Analysis PCTRIS03104743.

Karpuj et al. "Prolonged survival and decreased abnormal movements in transgenic model of Huntington disease, with administration of the transglutaminase inhibitor cystamine" Nature Med., Feb. 2002, pp. 143-149, vol. 8, Issue 2.

Keillor, J. "Tissue Transglutaminase Inhibition" Chem. & Biol., 2005, pp. 410-412, vol. 12.

Kim et al. "Transglutaminases in disease" Neurochem. Int., 2002, pp. 85-103, vol. 40.

Lahteenoja et al. "Local challenge on oral mucosa with an alpha-gliadin related synthetic peptide in patients with celiac disease" Am. J. Gastroenterol., 2000, pp. 2880, vol. 95.

Lion. *Flavobacterium meningosepticum*. Genbank Accession #/EMBL #: D10980. Aug. 1, 1992. http://www.infobiogen.fr/srs71bin/cgi-bin/wgetz?-id+4jqa61Mc9PO+[uniprot-ID:PPCE_FLAME]+-e.

Lorand et al. "Novel inhibitors against the transglutaminase-catalysed crosslinking of lens proteins" Exp Eye Res., May 1998, pp. 531-536, vol. 66.

Martinet et al. "In vivo transglutaminase type 1 expression in normal lung, preinvasive bronchial lesions, and lung cancer" Am J Respir Cell Mol Biol., Apr. 2003, pp. 428-435, vol. 28, Issue 4.

Messer et al. "Studies On The Mechanism Of Destruction Of The Toxic Action Of Wheat Gluten In Coeliac Disease By Crude Papain" Gut., Aug. 1964, pp. 295-303, vol. 5.

Messer et al. "Oral papain in gluten intolerance." Lancet, Nov. 6, 1976, p. 1022, vol. 2, Issue 7993.

Moodie, P. "Traditional Baking Enzymes-Proteases" Presented at the American Institute of Baking, Manhattan, Kansas, May 7, 2001 by Peter Moodie, Director—Sales & Marketing, Enzyme Development Corporation, Enzyme Development Corporation.

Online-Medical Dictionary. "Amino acid". http://cancerweb.ncl.ac.uk/cgi-bin/omd?query=amino+acid. Nov. 13, 1997.

Piper et al., "High selectivity of human tissue transglutaminase for immunoactive gliadin peptides: implications for celiac spure", Biochemistry, Jan. 8, 2002, pp. 386-393, vol. 41, Issue 1.

Piper, J., et al., "Effect of prolyl endopeptidase on digestive-resistant gliadin peptides in vivo," The Journal of Pharmacology and Experimental Therapeutics, 2004, pp. 213-219, vol. 311, Issue 1.

Sárdy, M. et al. "Epidermal transglutaminase (TGase 3) is the autoantigen of dermatitis herpetiformis" J. Exp. Med., 2002, pp. 747-757, vol. 195, Issue 6.

Schuppan et al. "Special Reports and Reviews: Current Concepts Of Celiac Disease Pathogenesis" Gastroenterology, 2000, pp. 234-242, vol. 119.

Shan, L. et al. "Structural Basis for Gluten Intolerance in Celiac Sprue" Science 2002, pp. 2275-2279, vol. 297.

Shan, L. et al. "Comparative biochemical analysis of three bacterial prolyl endopeptidases: implications of coeliac sprue," Biochem J, 2004, pp. 311-318, vol. 383.

Sjostrom et al. "Identification of a Gliadin T-Cell Epitope in Coeliac Disease: General Importance of Gliadin Deamidation for Intestinal T-Cell Recognition" Scandinavian Journal of Immunology, Aug. 1998, pp. 111-115(5), vol. 48, No. 2.

Stepniak, D. et al. "Highly efficient gluten degradation with a newly identified prolyl endoprotease: implications for celiac disease,"Am J Physiol Gastrointest Liver Physiol, 2006, pp. G621-G629, vol. 291.

Vader et al. "The Gluten Response in Children with Celiac Sprue Disease is Directed Toward Multiple Gliadin and Glutenin Peptides" Gastroenterology, 2002, pp. 1729-1737, vol. 122.

Vader et al. "The HLA-DQ2 Gene Dose Effect in Celiac Disease is Doirectly Related to the Magnitude and Breadth of Gluten-Specific T Cell Responses" PNAS, Oct. 14, 2003, pp. 12390-12395, vol. 123, No. 3.

Wieser "The Precipitating Factor In Coeliac Disease" Baillieres Clinical Gastroenterol, 1995, pp. 191-207, vol. 9, Issue 2.

Wiesner, "Relation Between Structure An Dcoeliac Toxicity" Acta Paediatr Suppl., 1996, pp. 3-9, vol. 412.

Yoshimoto et al., "Prolyl Endopeptidase From *Flavobacterium meningosepticum*: Cloning And Sequencing Of The Enzyme Gene" J. Biochem., 1991, pp. 873-878, vol. 110.

Zhang et al. "Identification of differentially expressed proteins in human glioblastoma cell lines and tumors" Glia., Apr. 15, 2003, pp. 194-208, vol. 42, Issue 2.

* cited by examiner

DRUG THERAPY FOR CELIAC SPRUE

CROSS-REFERENCE TO RELATED APPLICATIONS

This application claims priority to U.S. Provisional Application 60/380,761 filed May 14, 2002; to U.S. Provisional Application 60/392,782 filed Jun. 28, 2002; and to U.S. Provisional application No. 60/422,933, filed Oct. 31, 2002, and to U.S. Provisional Application 60/428,033, filed Nov. 20, 2002, each of which are herein specifically incorporated by reference.

This invention was made with Government support under contract 9910949 awarded by the National Science Foundation. The Government has certain rights in this invention.

BACKGROUND OF THE INVENTION

In 1953, it was first recognized that ingestion of gluten, a common dietary protein present in wheat, barley and rye causes a disease called Celiac Sprue in sensitive individuals. Gluten is a complex mixture of glutamine- and proline-rich glutenin and prolamine molecules and is thought to be responsible for induction of Celiac Sprue. Ingestion of such proteins by sensitive individuals produces flattening of the normally luxurious, rug-like, epithelial lining of the small intestine known to be responsible for efficient and extensive terminal digestion of peptides and other nutrients. Other clinical symptoms of Celiac Sprue include fatigue, chronic diarrhea, malabsorption of nutrients, weight loss, abdominal distension, anemia, as well as a substantially enhanced risk for the development of osteoporosis and intestinal malignancies such as lymphoma and carcinoma. The disease has an incidence of approximately 1 in 200 in European populations and is believed to be significantly under diagnosed in other populations.

A related disease is dermatitis herpetiformis, which is a chronic eruption of the skin characterized by clusters of intensely pruritic vesicles, papules, and urticaria-like lesions. IgA deposits occur in almost all normal-appearing and perilesional skin. Asymptomatic gluten-sensitive enteropathy is found in 75 to 90% of patients and in some of their relatives. Onset is usually gradual. Itching and burning are severe, and scratching often obscures the primary lesions with eczematization of nearby skin, leading to an erroneous diagnosis of eczema. Strict adherence to a gluten-free diet for prolonged periods may control the disease in some patients, obviating or reducing the requirement for drug therapy. Dapsone, sulfapyridine, and colchicines are sometimes prescribed for relief of itching.

Celiac Sprue (CS) is generally considered to be an autoimmune disease and the antibodies found in the serum of the patients support the theory that the disease is immunological in nature. Antibodies to tissue transglutaminase (tTGase or tTG) and gliadin appear in almost 100% of the patients with active CS, and the presence of such antibodies, particularly of the IgA class, has been used in diagnosis of the disease.

The large majority of patients express the HLA-DQ2 [DQ (a1*0501, b1*02)] and/or DQ8 [DQ(a1*0301, b1*0302)] molecules. It is believed that intestinal damage is caused by interactions between specific gliadin oligopeptides and the HLA-DQ2 or DQ8 antigen, which in turn induce proliferation of T lymphocytes in the sub-epithelial layers. T helper 1 cells and cytokines apparently play a major role in a local inflammatory process leading to villous atrophy of the small intestine.

At the present time, there is no good therapy for the disease, except to avoid completely all foods containing gluten. Although gluten withdrawal has transformed the prognosis for children and substantially improved it for adults, some people still die of the disease, mainly adults who had severe disease at the outset. A leading cause of death is lymphoreticular disease, especially intestinal lymphoma. It is not known whether a gluten-free diet diminishes this risk. Apparent clinical remission is often associated with histologic relapse that is detected only by review biopsies or by increased EMA titers.

Gluten is so widely used, for example, in commercial soups, sauces, ice creams, hot dogs, and other foodstuffs, that patients need detailed lists of foodstuffs to avoid and expert advice from a dietitian familiar with celiac disease. Ingesting even small amounts of gluten may prevent remission or induce relapse. Supplementary vitamins, minerals, and hematinics may also be required, depending on deficiency. A few patients respond poorly or not at all to gluten withdrawal, either because the diagnosis is incorrect or because the disease is refractory. In the latter case, oral corticosteroids (e.g., prednisone 10 to 20 mg bid) may induce response.

In view of the serious and widespread nature of Celiac Sprue and the difficulty of removing gluten from the diet, better methods of treatment are of great interest. In particular, there is a need for treatment methods that allow the Celiac Sprue individual to eat gluten-containing foodstuffs without ill effect or at least to tolerate such foodstuffs in small or moderate quantities without inducing relapse. The present invention meets this need for better therapies for Celiac Sprue by providing new drugs and methods and formulations of new and existing drugs to treat Celiac Sprue. International Patent Application US03/04743, herein specifically incorporated by reference, discloses aspects of gluten protease stability and immunogenicity.

SUMMARY OF THE INVENTION

In one aspect, the present invention provides methods for treating Celiac Sprue and/or dermatitis herpetiformis and the symptoms thereof by administration of a tTGase (tissue transglutaminase) inhibitor to the patient. In one embodiment, the tTGase inhibitor employed in the method is a known small molecule-tTGase inhibitor selected from the group consisting of vinylogous amides, sulfonamides, 2-[(2-oxoalkyl)thio] imidazolium compounds, diazoketones, and 3-halo-4,5-dihydroisoxazoles. In another embodiment, the tTGase inhibitor is a dipeptide mimetic, a compound that mimics in structure a dipeptide selected from the group consisting of PQ, PY, QL, and QP.

In another aspect, the present invention provides novel tTGase inhibitors and methods for treating Celiac Sprue and/or dermatitis herpetiformis by administering those compounds. In one embodiment, the tTGase inhibitor is a peptide or peptidomimetic that has or contains within a longer sequence the structure of the peptide PQPQLPY [SEQ ID NO:1] or PQPELPY [SEQ ID NO:2] in which the E or the second Q is replaced by a glutamine mimetic that is an inhibitor of tTGase or in which a dipeptide selected from the group consisting of QP and LP is replaced by a constrained dipeptide mimetic compound. Such compounds are analogs of a sequence contained in gluten oligopeptides that are resistant to digestion and are believed to stimulate the autoimmune reaction that characterizes Celiac Sprue.

In another aspect, the invention provides pharmaceutical formulations comprising a tTGase inhibitor and a pharmaceutically acceptable carrier. In one embodiment, such formulations comprise an enteric coating that allows delivery of the active agent to the intestine, and the agents are stabilized to resist digestion or acid-catalyzed modification in acidic stomach conditions. In another embodiment, the formulation also comprises one or more glutenases, as described in U.S. Provisional Application 60/392,782 filed Jun, 28, 2002; and U.S. Provisional Application 60/428,033, filed Nov. 20, 2002, both of which are incorporated herein by reference. The invention also provides methods for the administration of enteric formulations of one or more tTGase inhibitors to treat Celiac Sprue.

In another aspect, the invention provides methods for screening candidate compounds to determine their suitability for use in the subject methods, by assessing the ability of a candidate agent for its ability to bind to, and/or to inhibit the activity of, tTGase. Candidate agents may also be screened for anti-allergic and anti-inflammatory activity by assessing their ability to bind to, and/or to inhibit the activity of, tTGase.

In another aspect, the tTGase inhibitors and/or pharmaceutical formulations of the present invention are useful in treating disorders where TGases are a factor in the disease etiology, where such disorders may include cancer, neurological disorders, wound healing, etc. These conditions include Alzheimer's and Huntington's diseases, where the TGases appear to be a factor in the formation of inappropriate proteinaceous aggregates that may be cytotoxic. In diseases such as progressive supranuclear palsy, Huntington's, Alzheimer's and Parkinson's diseases, the aberrant activation of TGases may be caused by oxidative stress and inflammation.

These and other aspects and embodiments of the invention and methods for making and using the invention are described in more detail in the description of the drawings and the invention, the examples, the claims, and the drawings that follow.

DETAILED DESCRIPTION OF THE EMBODIMENTS

Celiac Sprue and/or dermatitis herpetiformis are treated by inhibition of tissue transglutaminase. Therapeutic benefit can be enhanced in some individuals by increasing the digestion of gluten oligopeptides, whether by pretreatment of foodstuffs to be ingested or by administration of an enzyme capable of digesting the gluten oligopeptides, together with administration of the tTGase inhibitor. Gluten oligopeptides are highly resistant to cleavage by gastric and pancreatic peptidases such as pepsin, trypsin, chymotrypsin, and the like, and their prolonged presence in the digestive tract can induce an autoimmune response mediated by tTGase. The antigenicity of gluten oligopeptides and the ill effects caused by an immune response thereto can be decreased by inhibition of tissue transglutaminase. In another embodiment of the invention, by also providing a means for digestion of gluten oligopeptides with glutenase, gluten oligopeptides are cleaved into fragments, thereby contributing to the prevention of the disease-causing toxicity.

Methods and compositions are provided for the administration of one or more tTGase inhibitors to a patient suffering from Celiac Sprue and/or dermatitis herpetiformis. In some embodiments and for some individuals, the methods of the invention remove the requirement that abstention from ingestion of glutens be maintained to keep the disease in remission. The compositions of the invention include formulations of tTGase inhibitors that comprise an enteric coating that allows delivery of the agents to the intestine in an active form; the agents are stabilized to resist digestion or alternative chemical transformations in acidic stomach conditions. In another embodiment, food is pretreated or combined with glutenase, or a glutenase is co-administered (whether in time or in a formulation of the invention) with a tTGase inhibitor of the invention.

The subject methods are useful for both prophylactic and therapeutic purposes. Thus, as used herein, the term "treating" is used to refer to both prevention of disease, and treatment of a pre-existing condition. The treatment of ongoing disease, to stabilize or improve the clinical symptoms of the patient, is a particularly important benefit provided by the present invention. Such treatment is desirably performed prior to loss of function in the affected tissues; consequently, the prophylactic therapeutic benefits provided by the invention are also important. Evidence of therapeutic effect may be any diminution in the severity of disease, particularly diminution of the severity of such symptoms as fatigue, chronic diarrhea, malabsorption of nutrients, weight loss, abdominal distension, and anemia. Other disease indicia include the presence of antibodies specific for glutens, antibodies specific for tissue transglutaminase, the presence of pro-inflammatory T cells and cytokines, and degradation of the villus structure of the small intestine. Application of the methods and compositions of the invention can result in the improvement of any and all of these disease indicia of Celiac Sprue.

Patients that can benefit from the present invention include both adults and children. Children in particular benefit from prophylactic treatment, as prevention of early exposure to toxic gluten peptides can prevent development of the disease into its more severe forms. Children suitable for prophylaxis in accordance with the methods of the invention can be identified by genetic testing for predisposition, e.g. by HLA typing; by family history, and by other methods known in the arL. As is known in the art for other medications, and in accordance with the teachings herein, dosages of the tTGase inhibitors of the invention can be adjusted for pediatric use.

Because most proteases and peptidases are unable to hydrolyze the amide bonds of proline residues, the abundance of proline residues in gliadins and related protiens from wheet, rye and barley can constitute a major digestive obstacle for the enzymes invovled. This leads to an increased concentration of relatively stable gluten derived oligopeptides in the gut. These stable gluten derived oligopeptides, called "toxic oligpeptides" herein, interact with tTGase to stimulate an immune response that results in the autoimmune disease aspects of Celiac Sprue.

Such toxic oligopeptides include the peptide sequence PQPQLPY [SEQ ID NO:1] and longer peptides containing that sequence or multiple copies of that sequence. This peptide sequence is a high affinity substrate for the enzyme tissue transglutaminase (tTGase), an enzyme found on the extracellular surface in many organs including the intestine. The tTGase enzyme catalyzes the formation of isopeptide bonds between glutamine and lysine residues of different polypeptides, leading to protein-protein crosslinks in the extracellular matrix. The tTGase enzyme acts on the peptide sequence PQPQLPY [SEQ ID NO:1] to deamidate the second Q residue, forming the peptide sequence PQPELPY [SEQ ID NO:2]. The tTGase enzyme is the primary focus of the autoantibody response in Celiac Sprue. Gliadins, secalins and hordeins contain several of the PQPQLPY [SEQ ID NO:1] sequences or sequences similar thereto rich in Pro-Gln residues that are high-affinity substrates for tTGase. The tTGase catalyzed deamidation of such sequences dramatically increases their affinity for HLA-DQ2, the class II MHC allele present in >90% Celiac Sprue patients. Presentation of these deamidated sequences by DQ2 positive antigen presenting cells effectively stimulates proliferation of gliadin-specific T cells from intestinal biopsies of most Celiac Sprue patients, providing evidence for the proposed mechanism of disease progression in Celiac Sprue.

There are a number of known tTGase inhibitors that can be used in the methods of the invention. While known, these compounds have never before been used to treat Celiac Sprue effectively, because the compounds have not been administered to Celiac Sprue patients in the formulations and dosages required to deliver the active inhibitor to the small intestine in efficacious amounts. Known tTGase inhibitors include certain glutamine mimetic compounds, including compounds selected from the group consisting of vinylogous amides, sulfonamides, diazoketones, 3-halo-4, 5-dihydroisoxazoles, and 1,2,4-thiadiazoles. While the present invention is not to be bound by a mechanistic theory, it is believed that these compounds provide an effective therapy for Celiac Sprue by reversibly or irreversibly inhibiting the tTGase in the small intestine, thereby preventing it from acting on the oligopeptides comprising the PQPQLPY [SEQ ID NO:1] sequence.

PQPQLPY [SEQ ID NO:1] is a high affinity substrate for tTGase, because it has a structure that is highly complementary to the structure of the active site of the tTGase enzyme. In particular, the peptide bonds preceding Pro residues adopt trans configurations, thereby allowing the peptide to adopt an extended polyproline II helical structure. This polyproline II helical character is a general property of immunogenic gliadin peptides, and is an important determinant of their high affinity toward tTGase. Therefore, it has been exploited in the design of certain tTGase inhibitors of the invention. By administering compounds that bind to the active site of the tTGase enzyme and prevent either the binding of immunogenic gliadin peptides such as the 33-mer LQLQPF-PQPQLPYPQPQLPYPQPQLPYPQPQPF [SEQ ID NO:3], or their conversion to regioselectively deamidated products, a therapeutic benefit can be achieved in Celiac Sprue patients. In part, the present invention arises out of the discoveries that the dipeptides QP and LP play an important role in forming the structure that binds to the active site of the tTGase enzyme and that compounds that mimic the configurations of these dipeptides in a polyproline helix (i.e. where the imide bond adopts a trans configuration) can be used to inhibit tTGase and treat Celiac Sprue. Thus, in addition to the methods for administering the glutamine mimetic compounds described above, the present invention provides methods in which a small organic molecule that is a constrained mimetic of a dipeptide selected from the group consisting of PQ, QP, PE, PY, and LP is administered to a Celiac Sprue patient to treat celiac disease.

The tTGase inhibitors of the present invention that have structures that mimic the conformation of the key dipeptide moieties of the tTGase substrate can be thought of as "tTGase inhibitory motif" or "tTGase inhibitory moiety". Human tTGase has a strong preference for peptide substrates with Type II polyproline character. This conformational preference is exploited by the selective tTGase inhibitors of the invention. Dipeptide moieties of interest have the formula XP, wherein X can be any amino acid but is preferably selected from the group consisting of Q, Y, L, E, or F. Inhibitors of the invention containing such moieties are referred to as "peptide mimetics" or "peptidomimetics".

Examples of dipeptidomimetics based on the trans-PQPQLPY [SEQ ID NO:1] peptide are shown below.

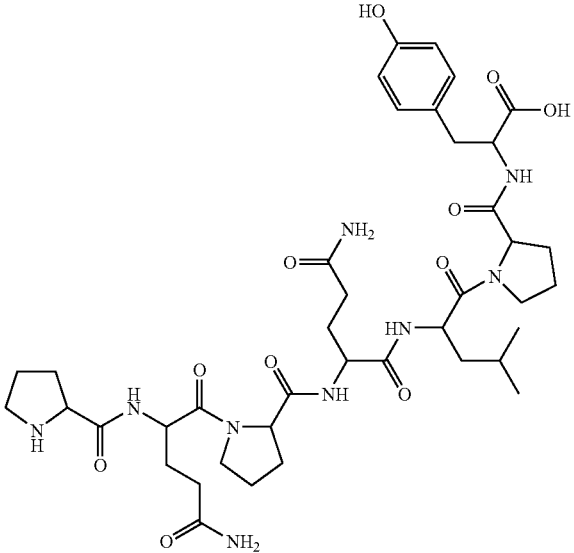

trans-PQPQLPY (all X—P bonds in trans configuration)

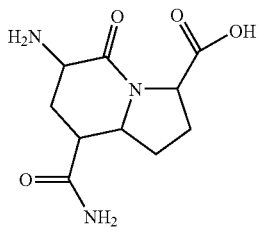

QP dipeptidomimetic

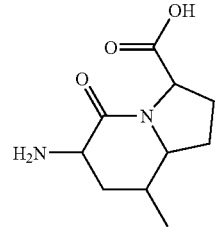

LP dipeptidomimetic

Similar dipeptidomimetics can be identified based on sequences of other high-affinity gliadin peptide substrates of tTGase. Common constrained dipeptide mimetics useful for purposes of the invention also include quinozilidinone, pyrroloazepinone, indolizidinone, alkylbranched azabicyclo [X.Y.0]alkane amino acids (Gosselin et al., *J. Org. Chem.* 2000, 65, 2163-71; Polyak et al., *J. Org. Chem.* 2001, 66, 1171-80), 6,5-fused bicyclic lactam (Mueller et al., *Tetrahedron Lett.* 1994, 4091-2; Dumas, *Tetrahedron Lett.*1994, 1493-6, and Kim, 1997, *J. Org. Chem.* 62, 2847-52 ), and lactam methylene linker.

The dipeptide mimetic tTGase inhibitor compounds, like the glutamine mimetic tTGase inhibitor compounds, are believed to provide a therapeutic benefit to Celiac Sprue patients by preventing tTGase from binding the toxic oligopeptide comprising the PQPQLPY [SEQ ID NO:1]

sequence and converting it to the PQPELPY [SEQ ID NO:2] sequence, thus preventing the initiation of the autoimmune response responsible for the symptoms of the disease. Alternatively, these dipeptidomimetics can be incorporated into a PQPQLPY [SEQ ID NO:1] sequence or longer peptide or peptidomimetic containing that sequence in place of the corresponding dipeptide moiety. It is well understood in the pharmaceutical arts that the more selective a drug for its intended target, and the greater affinity of a drug for its intended target, the more useful the drug for the treatment of the disease relating to that target. Thus, while the glutamine and dipeptide mimetic inhibitors of the invention can be used to treat Celiac Sprue, there will in some instances be a need for or benefit from compounds with greater specificity for and affinity to tTGase. The present invention provides such compounds.

Thus, while beneficial therapeutic effect can be achieved by delivery of any tTGase inhibitor to the small intestine of a Celiac Sprue patient, in a preferred embodiment, the tTGase inhibitor is contained in a molecule that is a high affinity peptide or peptidomimetic substrate of tTGase or a peptidomimetic thereof. Thus, the inhibitors of tTGase provided by the present invention include modified high affinity peptide substrates for tTGase, where one or more glutamine residues of the peptide substrate are substituted with tTGase inhibitory moieties or one or more dipeptides in the substrate are substituted with a dipeptide mimetic or both. In either event, the peptide or peptidomimetic does not induce an autoimmune response in the Celiac Sprue patient.

High affinity peptide substrates for tTGase include the following peptides, and, with respect to the larger peptides shown, fragments thereof: PQPQLPY [SEQ ID NO:1], PQPQLPYPQPQLP [SEQ ID NO:4]; LQLQPF-PQPQLPYPQPQLPYPQPQLPYPQPQPF [SEQ ID NO:3]; QPQPFPPQLPYPQTQPFPPQQPYPQPQPQYPQPQ (from α1- and α6-gliadins) [SEQ ID NO:6]; QQQPF-PQQPIPQQPQPYPQQPQPYPQQPFPPQQPF (from B1 hordein) [SEQ ID NO:7]; QPFPQPQQTFPQQPQLPF-PQQPQQPFPQPQ (from y-gliadin) [SEQ ID NO:8]; VQW-PQQQPVPQPHQPF (from y-gliadin) [SEQ ID NO:9], VQGQGIIQPQQPAQ (from y-gliadin) [SEQ ID NO:10], FLQPQQPFPQQPQQPYPQQPQQPFPQ (from y-gliadin) [SEQ ID NO:11], FSQPQQQFPQPQQPQQSFPQQQPP (from y-gliadin) [SEQ ID NO:12], and QPFPQPQQPT-PIQPQQPFPQRPQQPFPQPQ [SEQ ID NO:13]. These peptides are resistant toward endo- and exo-proteolysis by gastric, pancreatic and small intestinal enzymes. Conservative amino acid substitutions, such as Y ->F, Q ->N/E, or L ->M, are also tolerated. Therefore, in accordance with the present invention, selective inhibitors of tTGase are provided by substituting either a glutamine that is deamidated by tTGase or a dipeptide contained in the peptide that binds in the active site of tTGase with a mimetic such that the resulting compound is an inhibitor of tTGase that does not stimulate the autoimmune response in a Celiac Sprue patient.

The reactive glutamines in the above proteolytically stable peptides include those glutamines identified as "(Q->E)", E being the amino acid formed by deamidation of glutamine, in the following sequences: PQP(Q->E)LPY [SEQ ID NO:15], PQP (Q->E) LPYPQPQLP [SEQ ID NO:16]; LQLQPFPQP (Q->E)LPYPQPQLPYPQP(Q->E) LPYPQPQPF [SEQ ID NO:17], FSQP(Q->E)Q(Q->E)FPQPQQPQQSFP(Q->E)Q (Q->E) PP [SEQ ID NO:18], VQGQGIIQP(Q->E)QPAQ [SEQ ID NO:19], and FLQPQQPFP(Q->E)QP(Q->E) QPYPQOPQQPFPQ [SEQ ID NO:20]. Reactive glutamine residues in other peptides can be identified by standard HPLC-MS-MS procedures, and can be replaced by glutamine mimetics. The (Q->E) residues can be replaced by glutamine mimetics and/or the OP and LP dipeptides in these sequences can be replaced by dipeptidomimetics as discussed above. The novel tTGase inhibitors of the invention are peptides or peptidomimetic compounds in which either a reactive glutamine or a dipeptide that binds in the active site of tTGase or both has been replaced by a small molecule mimetic are referred to herein as "substituted peptides". In one embodiment, the tTGase inhibitors useful in the methods and compositions of the present invention are those for which the affinity of the inhibitory moiety for the tTG active site increases (as measured by a decrease in $K_I$, or an increase in $k_{inh}/K_I$) when presented in the context of a high affinity, proteolytically stable peptide substrate of the enzyme. This aspect of the invention is illustrated in the Examples below.

Such compounds of the invention are illustrated below by compounds in which a reactive glutamine is replaced by a tTGase inhibitory moiety. Various tTGase inhibitory moieties useful in the methods of the invention and that are incorporated into the novel substituted peptide and peptidomimetic tTGase inhibitors of the invention include the following compounds, which are shown with variable (designated R) groups to indicate that the compounds can be used directly as small molecule inhibitors or incorporated into a larger dipeptide mimetic or peptide or peptidomimetic tTGase inhibitory compound of the invention.

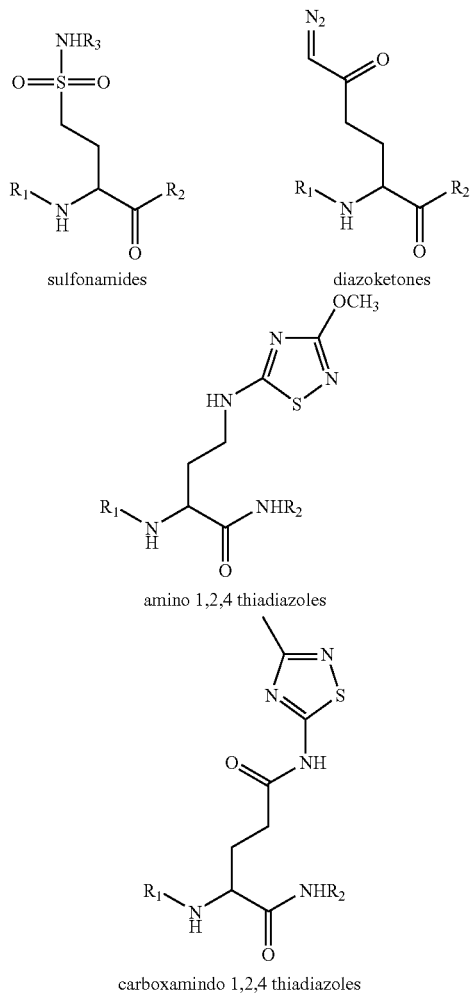

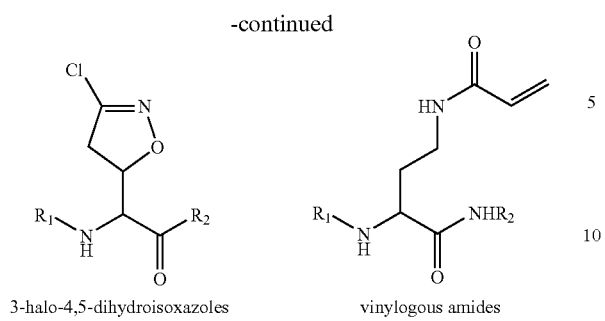

3-halo-4,5-dihydroisoxazoles      vinylogous amides

In the compounds shown above, R1, R2 and R3 are independently selected from H, alkyl, alkenyl, cycloalkyl, aryl, heteroalkyl, heteroaryl, alkoxy, alkylthio, arakyl, aralkenyl, halo, haloalkyl, haloalkoxy, heterocyclyl, and heterocyclylalkyl groups. R1 and R2 can also be an amino acid, a peptide, a peptidomimetic, or a peptidic protecting groups. Illustrative functional groups include: $R_1$ is selected from the group consisting of Cbz, Fmoc, Boc, PQP, Ac-PQP, PQPQLPYPQP [SEQ ID NO:21], Ac-PQPQLPFPQP [SEQ ID NO:22], QLQPFPQOP [SEQ ID NO:23], LQLQPFPQPLPYPQP [SEQ ID NO:24], $X_{2-15}$—P (where $X_{2-15}$ is a peptide consisting of any 2-15 amino acid residues followed by a N-terminal proline); and $R_2$ is selected from the group consisting of OMe, OtBu, Gly, Gly-NH$_2$, LPY, LPF-NH$_2$, LPYPQPQLPY [SEQ ID NO:25], LPFPQPQLPF-NH$_2$ [SEQ ID NO:26], LPYPQPQLP [SEQ ID NO:27], LPYPQPQLPYPQPQPF [SEQ ID NO:28], LP-$X_{2-15}$ (where $X_{2-15}$ is a peptide consisting of any 2-15 amino acid residues followed by a C-terminal proline).

Given the high selectivity of human tTGase for the peptide Ac-PQPQLPF-NH$_2$ [SEQ ID NO:29], and

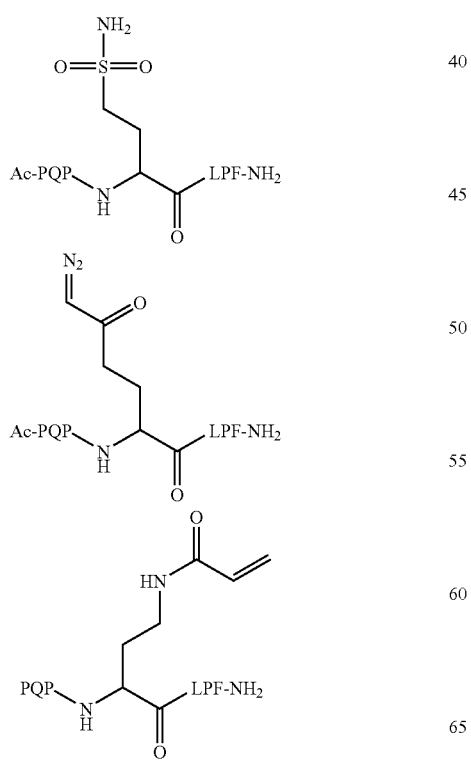

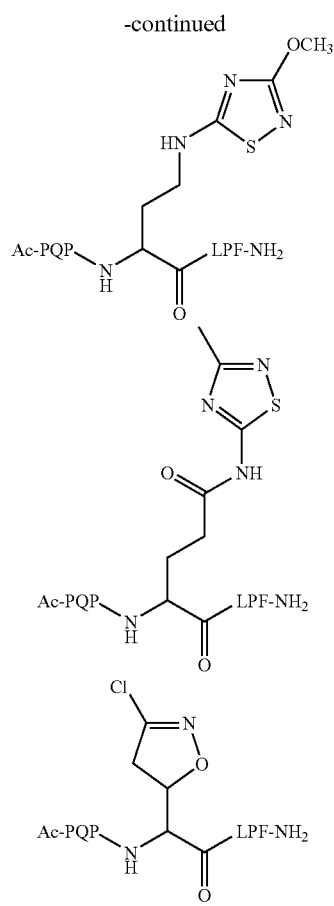

the intrinsic resistance of this peptide toward gastrointestinal proteolysis, the following tTGase inhibitors are provided by the present invention.

In each case, an inhibitor of the invention with greater specificity is provided by individual or combinatorial substitution of Q, L and F with alternative amino acids. In the case of sulfonamide inhibitors, the following analogs are also provided, where R is selected from an alkyl, alkenyl, cycloalkyl, aryl, heteroalkyl, heteroaryl, alkoxy, alkylthio, arakyl, aralkenyl, halo, haloalkyl, haloalkoxy, heterocyclyl, or heterocyclylalkyl group. Of particular interest are the sulfonyl hydrazides (R=NHR') where R' is H. alkyl, alkenyl, cycloalkyl, aryl, heteroalkyl, heteroaryl, alkoxy, alkylthio, arakyl, aralkenyl, halo, haloalkyl, haloalkoxy, heterocyclyl, or heterocyclylalkyl group.

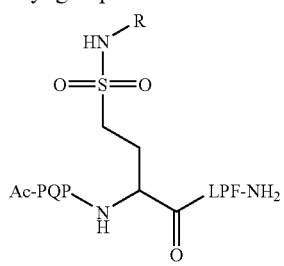

In one preferred embodiment, R is a functional group whose corresponding amine is a preferred nucleophilic co-substrate of human tTGase. For example, the biological amine histamine is an excellent co-substrate of tGase (kcat=20 min$^{-1}$, KM=40 μM). Consequently, the following compound is a preferred tTGase inhibitor of this invention:

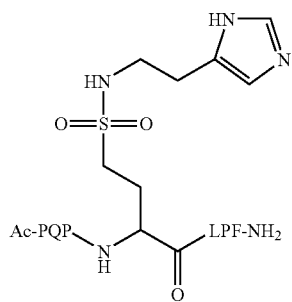

The synthesis of such compounds of the invention can be carried out using methods known in the art for other purposes and the teachings herein. For example, the synthesis of vinylogous amides such as 1 (see the numbered structure shown below) containing an acrylamide function have been reported by Macedo et al. (*Bioorg. Med. Chem.* (2002) 10, 355-360). Their ability to inhibit guinea pig tTG has been demonstrated (Marrano et al., *Bioorg. Med. Chem.* (2001)9, 3231-3241). Illustrative vinylogous amide compounds of the invention include compounds in which a glutamine mimetic with an acrylamide motif such as 2 (see the numbered structure below) is contained in a peptide or peptidomimetic having the following structures: $R_1$ is selected from the group consisting of PQP, Ac-PQP, PQPQLPYPQP [SEQ ID NO:21], Ac-PQPQLPFPQP [SEQ ID NO:22], QPFPQP [SEQ ID NO:30], LQLQPFPQPLPYPQP [SEQ ID NO:24], or an amino acid protecting group, including but not limited to Boc and Fmoc; and $R_2$ is selected from the group consisting of LPY, LPF-NH$_2$, LPYPQPQLPY [SEQ ID NO:25], LPF-PQPQLPF-NH$_2$ [SEQ ID NO:26], LPYPQPQ [SEQ ID NO:31], LPYPQPQLP [SEQ ID NO:27], LPYPQPQLPYPQPQPF [SEQ ID NO:28], or an amino acid protecting group, including but not limited to OtBu, OFm or additionally OBn or OMe.

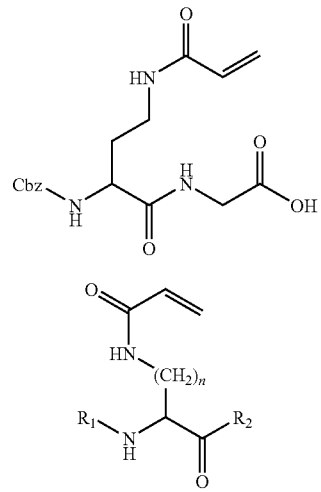

The acrylamides can be incorporated into a high affinity peptide of the invention by fragment condensation as illustrated below in a synthetic method of the invention using intermediate compounds of the invention.

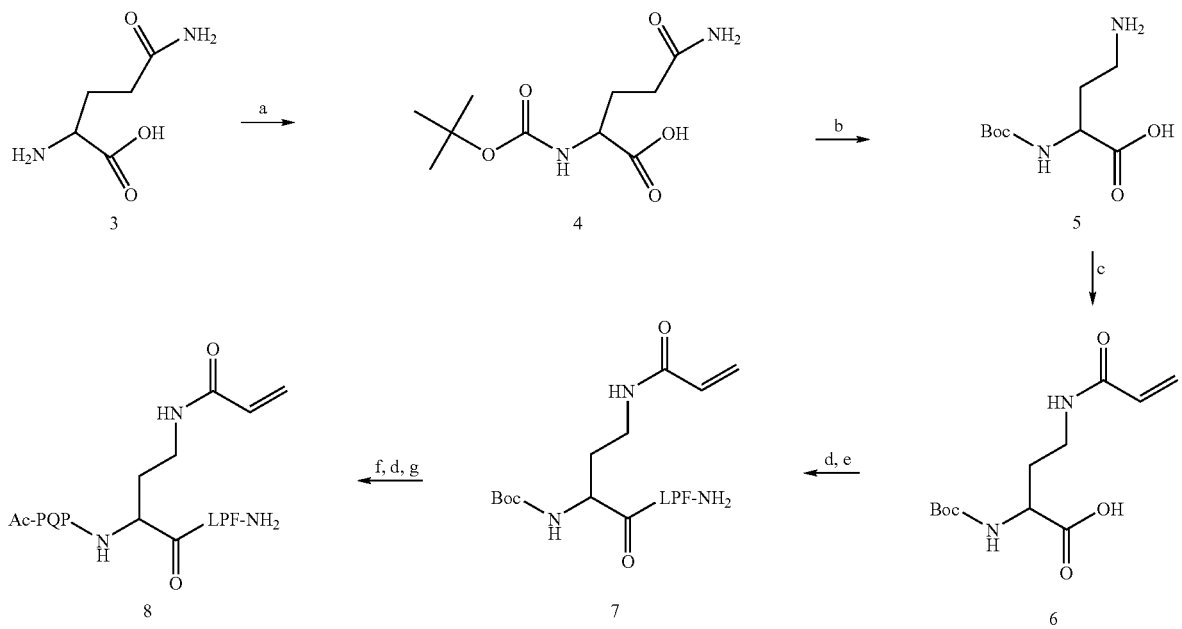

a  Boc$_2$O, RT, 4 h, Na$_2$CO$_3$/dioxane, 95%
b  C$_6$H$_5$(OCOCF$_3$)$_2$, pyridine, DMF/H$_2$O, RT, 3 h, 80%
c  acryl chloride, MeOH/TEA, 0° C.-RT, 12 h
d  EDC, TEA, DCM
e  LPF-NH$_2$, RT 12 h
f  HCl (gaseous), DCM, RT, 4 h
g  Ac-PQP, RT 12 h.

The tTGase inhibitory compounds of the invention from the sulfonamides, diazoketones, 1,2,4 thiadiazoles, and isoxazoles can likewise be readily prepared using methods known in the art for other purposes and the teachings herein. To illustrate the invention with respect to such classes of compounds, the following amino acid analogs are employed: 4-sufonamido-2-amino-butyric acid (Sab), 6-diazo-5-oxo-norleucine (Don), and acivicin (Aci),. These compounds are useful tTGase inhibitors without further modification, and novel tTGase inhibitors of the invention comprise the structures of these compounds as part of a larger, high affinity inhibitor of tTGase, as illustrated by the structures above.

Any high affinity tTGase substrate can be used to provide the scaffold for presenting a tTGase inhibitor moiety. Moreover, compounds not known to be tTGase substrates can be identified by screening peptide libraries, for example on chips or beads or displayed on phages using reporter groups such as dansyl- or biotinyl-cadaverine, using procedures known in the art. Additionally, the tTGase inhibitors of the invention can include other moieties. As one example, in some embodiments, the tTGase inhibitor further comprise one or more proline residues C- and/or N-terminally of the glutamine mimetic-containing peptides to block exoproteolytic degradation.

To illustrate various tTGase inhibitors of the invention, a variety of relatively small and large inhibitors were synthesized and tested for inhibitory activity. As examples of small molecule inhibitors, Z-Don-OMe and Z-Sab-Gly-OH were synthesized. As examples of larger inhibitors, the compounds Ac-PQP-X-LPF-NH$_2$ [SEQ ID NO:32], where X was Sab, a diazoketone, or acivicin, were synthesized.

Thus, Z-Don-OMe was synthesized as described (Allevi & Anatasia, *Tetrahedron Asymmetry* (2000) 11, 3151-3160; Pettit & Nelson, *Can. J. Chem.* (1986) 64, 2097-2102; Bailey & Bryans, *Tetrahedron Lett.* (1988) 29, 2231-2234). For the synthesis of Z-Sab-Gly-OH 33, commercially available racemic homocysteine thiolactone 24 was first protected to give 25 and subsequently saponified and acetylated in situ to give the free racemic acid 26 in high yield. Its coupling with the glycine benzyl ester 30 provided the dipeptide 31. Then, the conversion to the sulfonamide 32 was achieved via chlorination of the thioacetate moiety to a sulfonamide intermediate, followed by treatment with ammonia in CHCl$_3$. Finally, the benzyl ester protecting group was removed by saponification with an aqueous NaOH solution.

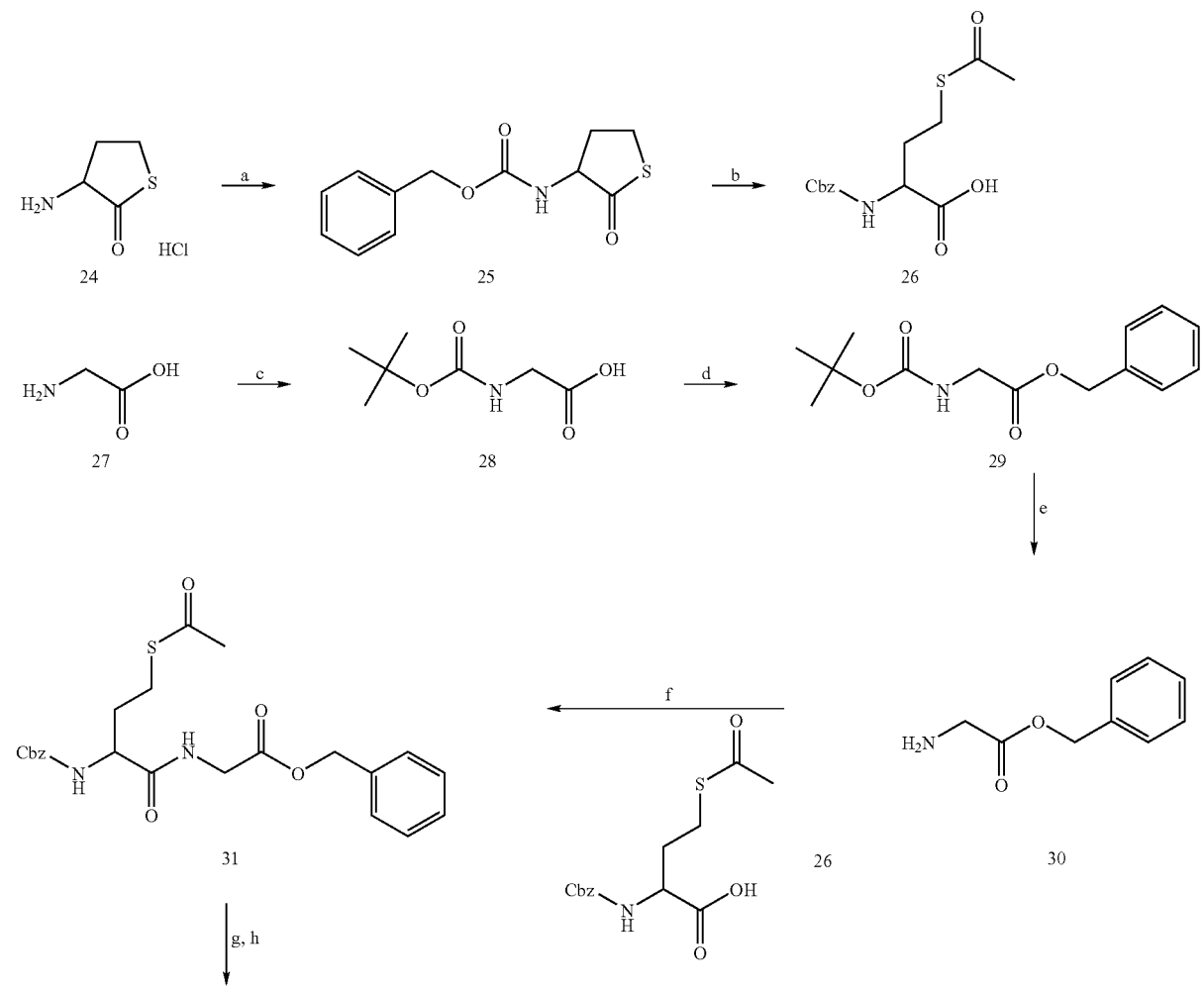

-continued

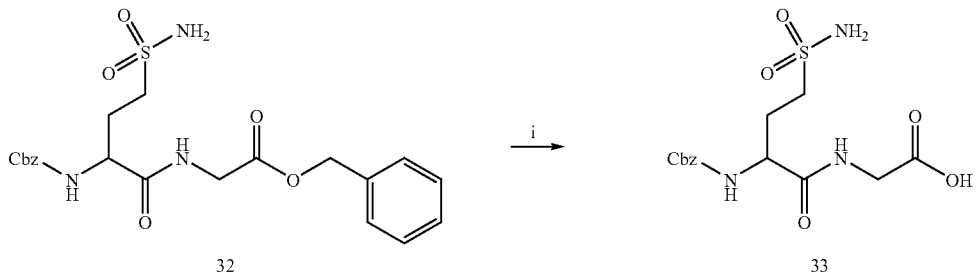

a Cbz-Cl, Na₂CO₃, H₂O, RT, 20 h, 95%.
b KOH, H₂O, then excess Ac₂O, 85%.
c BocOBoc, Na₂CO₃, H₂O:Dioxane, RT, 16 h, 98%.
d BnCO₂Cl, Et₃N, DCM, DMAP, 0° C., 30 min., 90%
e TFA 50% in DCM, RT, 2 h, 95%. (f). HOBT, EDPI, DMAP, DCM, RT, 20 h, 75%.
g Cl₂(g), AcOH, NaOAc, H₂O, T<10° C., 10 min.
h NH₃(g), CHCl₃, RT, 16 h, 75%.
i aq. NaOH, EtOH, RT, 4 h, 60%.

The sulfonamide building block (Sab) 9 was incorporated into the Ac-PQP-X-LPF-NH$_2$ scaffold by fragment condensation as illustrated in the following scheme:

The sulfonamide building block (Sab) 9 was incorporated into the Ac-PQP-X-LPF-NH2 [SEQ ID NO:32] scaffold by fragment condensation as illustrated in the following scheme:

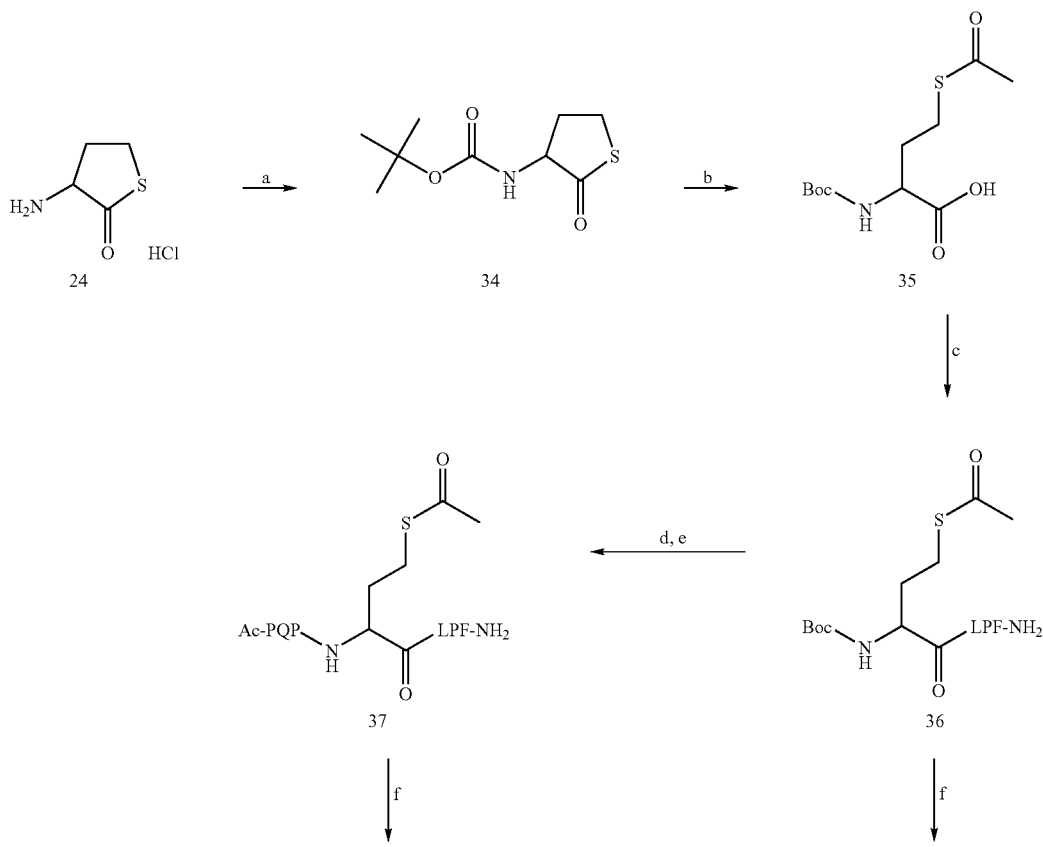

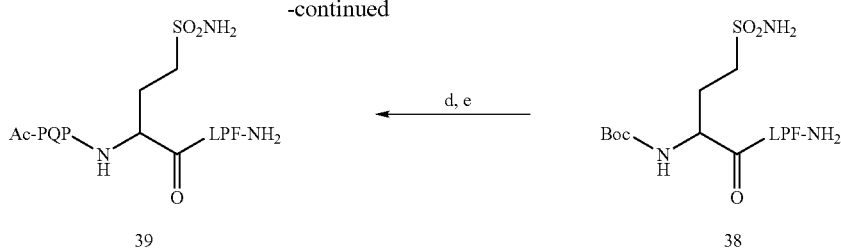

a Boc₂O, RT, 4 h, Na₂CO₃/dioxane, 95%
b KOH, H₂O, then excess Ac₂O, 85%; chiral resolution
c EDPI, TEA, DCM; LPF-NH₂, RT, 12 h
d HCl (g), DCM, RT, 4 h
e EDPI, TEA, DCM; Ac-PQP, RT, 12 h
f 1. Cl₂ (g), AcOH, NaOAc, H₂O, T<10° C., 10 min. 2. NH₃ (g), CHCl₃, RT, 16 h, 75%

The diazo-ketone 10a motif was introduced into the same scaffold by post-synthetic modification of Ac-PQP-Glu-LPF-NH₂ [SEQ ID NO:34] 40 to yield compound 41.

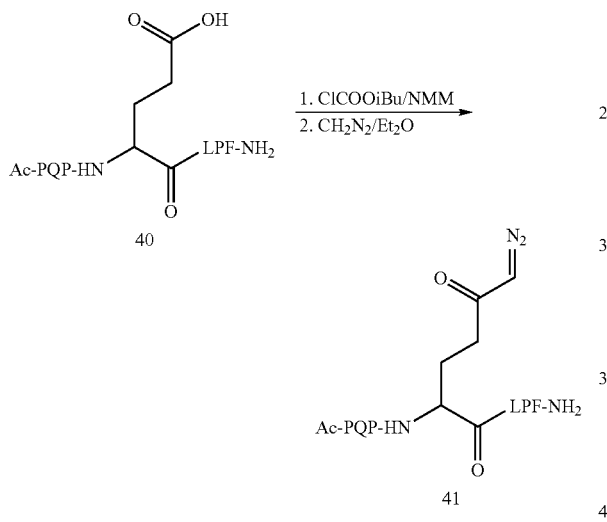

Incorporation of the acivicin moiety 12 into the high affinity PQPXLPY [SEQ ID NO:35] scaffold was achieved by Fmoc-protection of commercially available acivicin and Fmoc-compatible solid phase peptide chemistry as outlined below.

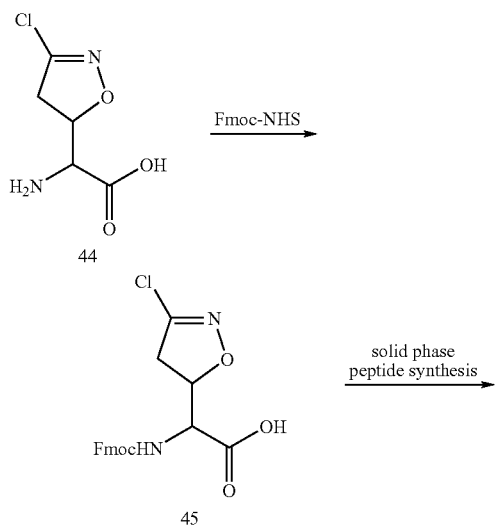

-continued

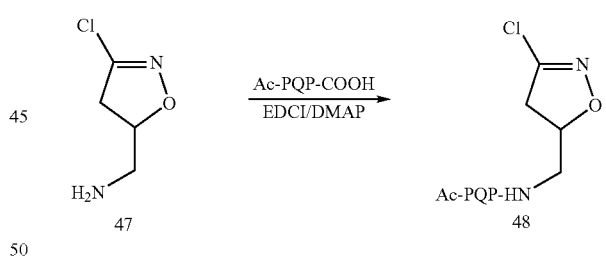

Synthesis of peptides containing 1,2,4 thiadiazoles is described by Marrano et al., Bioorg. Med. Chem. 9, 3231-3241 (2001). Because the carboxyl group of acivicin is not needed for tTG inhibition (Killackey et al., Mol. Pharmacol. (1989) 35, 701-706), the 3-chloro-4,5-dihydro-5-amino-isoxazole (Cai) group 13 was synthesized as described (Castelhano et al., Bioorg. Chem. (1988) 16, 335-340) and coupled C-terminally to a high-affinity peptide as depicted below:

The illustrative compounds of the invention described above were tested in a tTGase assay with recombinant human tissue transglutaminase, which was expressed, purified and assayed as described (Piper et al., Biochemistry (2001) 41, 386-393). Competitive inhibition with respect to the Cbz-Gln-Gly substrate was observed for all substrates; in all cases except for the Sab derivatives, irreversible inactivation of the enzyme was also observed. Importantly, all glutamine mimetics described above showed significant improved specificity within a tTG-specific peptide context. The results also demonstrated that, while the small molecule inhibitors can be used to inhibit tTGase, the larger compounds that present the glutamine mimetic tTGase inhibitor in the context of a peptide based on the PQPQLPY [SEQ ID NO:1] sequence tended to be better inhibitors.

Thus, the present invention provides a variety of different classes of known and novel tTGase inhibitors. To facilitate an appreciation of the invention, the tTGase inhibitors of the invention have in part been described above with structures containing variable "R" groups that are defined by reference to the various organic moieties that can be present at the indicated position in the structure. Below, brief definitions are provided for the phrases used to define the organic moieties listed for each R group.

As used herein, "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, 1,1-dimethylethyl (t-butyl), and the like. Unless stated otherwise specifically in the specification, the alkyl radical may be optionally substituted by hydroxy, alkoxy, aryloxy, haloalkoxy, cyano, nitro, mercapto, alkylthio, —N($R^8$)$_2$, —C(O)O$R^8$, —C(O)N($R^8$)$_2$ or —N($R^8$)C(O)$R^8$ where each $R^8$ is independently hydrogen, alkyl, alkenyl, cycloalkyl, cycloalkylalkyl, aralkyl or aryl. Unless stated otherwise specifically in the specification, it is understood that for radicals, as defined below, that contain a substituted alkyl group that the substitution can occur on any carbon of the alkyl group.

"Alkoxy" refers to a radical of the formula —O$R_a$ where $R_a$ is an alkyl radical as defined above, e.g., methoxy, ethoxy, n-propoxy, 1-methylethoxy (isopropoxy), n-butoxy, n-pentoxy, 1,1-dimethylethoxy (t-butoxy), and the like. Unless stated otherwise specifically in the specification, it is understood that for radicals, as defined below, that contain a substituted alkoxy group that the substitution can occur on any carbon of the alkoxy group. The alkyl radical in the alkoxy radical may be optionally substituted as described above.

"Alkylthio" refers to a radical of the formula —S$R_a$ where $R_a$ is an alkyl radical as defined above, e.g., methylthio, ethylthio, n-propylthio, 1-methylethylthio (iso-propylthio), n-butylthio, n-pentylthio, 1,1-dimethylethylthio (t-butylthio), and the like. Unless stated otherwise specifically in the specification, it is understood that for radicals, as defined below, that contain a substituted alkylthio group that the substitution can occur on any carbon of the alkylthio group. The alkyl radical in the alkylthio radical may be optionally substituted as described above.

"Alkenyl" refers to a straight or branched hydrocarbon chain radical consisting solely of carbon and hydrogen atoms, containing at least one double bond, having from two to eight carbon atoms, and which is attached to the rest of the molecule by a single bond or a double bond, e.g., ethenyl, prop-1-enyl, but-1-enyl, pent-1-enyl, penta-1,4-dienyl, and the like. Unless stated otherwise specifically in the specification, the alkenyl radical may be optionally substituted by hydroxy, alkoxy, haloalkoxy, cyano, nitro, mercapto, alkylthio, cycloalkyl, —N($R^8$)$_2$, —C(O)O$R^8$, —C(O)N($R^8$)$_2$ or —N($R^8$)—C(O)—$R^8$ where each $R^8$ is independently hydrogen, alkyl, alkenyl, cycloalkyl, cycloalkylalkyl, aralkyl or aryl. Unless stated otherwise specifically in the specification, it is understood that for radicals, as defined below, that contain a substituted alkenyl group that the substitution can occur on any carbon of the alkenyl group.

"Aryl" refers to a phenyl or naphthyl radical. Unless stated otherwise specifically in the specification, the term "aryl" or the prefix "ar-" (such as in "aralkyl") is meant to include aryl radicals optionally substituted by one or more substituents selected from the group consisting of hydroxy, alkoxy, aryloxy, haloalkoxy, cyano, nitro, mercapto, alkylthio, cycloalkyl, —N($R^8$)$_2$, —C(O)O$R^8$, —C(O)N($R^8$)$_2$ or —N($R^8$)C(O)$R^8$ where each $R^8$ is independently hydrogen, alkyl, alkenyl, cycloalkyl, cycloalkylalkyl, aralkyl or aryl.

"Aralkyl" refers to a radical of the formula -$R_a R_b$ where $R_a$ is an alkyl radical as defined above and $R_b$ is one or more aryl radicals as defined above, e.g., benzyl, diphenylmethyl and the like. The aryl radical(s) may be optionally substituted as described above.

"Aralkenyl" refers to a radical of the formula -$R_c R_b$ where $R_c$ is an alkenyl radical as defined above and $R_b$ is one or more aryl radicals as defined above, e.g., 3-phenylprop-1-enyl, and the like. The aryl radical(s) and the alkenyl radical may be optionally substituted as described above.

"Alkylene chain" refers to a straight or branched divalent hydrocarbon chain consisting solely of carbon and hydrogen, containing no unsaturation and having from one to eight carbon atoms, e.g., methylene, ethylene, propylene, n-butylene, and the like. The alkylene chain may be optionally substituted by one or more substituents selected from the group consisting of aryl, halo, hydroxy, alkoxy, haloalkoxy, cyano, nitro, mercapto, alkylthio, cycloalkyl, —N($R^8$)$_2$, —C(O)O$R^8$, —C(O)N($R^8$)$_2$ or —N($R^8$)C(O)$R^8$ where each $R^8$ is independently hydrogen, alkyl, alkenyl, cycloalkyl, cycloalkylalkyl, aralkyl or aryl. The alkylene chain may be attached to the rest of the molecule through any two carbons within the chain.

"Alkenylene chain" refers to a straight or branched divalent hydrocarbon chain consisting solely of carbon and hydrogen, containing at least one double bond and having from two to eight carbon atoms, e.g., ethenylene, prop-1-enylene, but-1-enylene, pent-1-enylene, hexa-1,4-dienylene, and the like. The alkenylene chain may be optionally substituted by one or more substituents selected from the group consisting of aryl, halo, hydroxy, alkoxy, haloalkoxy, cyano, nitro, mercapto, alkylthio, cycloalkyl, —N($R^8$)$_2$, —C(O)O$R^8$, —C(O)N($R^8$)$_2$ or —N($R^8$)C(O)$R^8$ where each $R^8$ is independently hydrogen, alkyl, alkenyl, cycloalkyl, cycloalkylalkyl, aralkyl or aryl. The alkenylene chain may be attached to the rest of the molecule through any two carbons within the chain.

"Cycloalkyl" refers to a stable monovalent monocyclic or bicyclic hydrocarbon radical consisting solely of carbon and hydrogen atoms, having from three to ten carbon atoms, and which is saturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents independently selected from the group consisting of alkyl, aryl, aralkyl, halo, haloalkyl, hydroxy, alkoxy, haloalkoxy, cyano, nitro, mercapto, alkylthio, cycloalkyl, —N($R^8$)$_2$, —C(O)O$R^8$, —C(O)N($R^8$)$_2$ or —N($R^8$)C(O)$R^8$ where each $R^8$ is independently hydrogen, alkyl, alkenyl, cycloalkyl, cycloalkylalkyl, aralkyl or aryl.

"Cycloalkylalkyl" refers to a radical of the formula -$R_a R_d$ where $R_a$ is an alkyl radical as defined above and $R_d$ is a cycloalkyl radical as defined above. The alkyl radical and the cycloalkyl radical may be optionally substituted as defined above.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Haloalkoxy" refers to a radical of the formula —O$R_c$ where $R_c$ is an haloalkyl radical as defined above, e.g., trifluoromethoxy, difluoromethoxy, trichloromethoxy, 2,2,2-trifluoroethoxy, 1-fluoromethyl-2-fluoroethoxy, 3-bromo-2-fluoropropoxy, 1-bromomethyl-2-bromoethoxy, and the like.

"Heterocyclyl" refers to a stable 3- to 15-membered ring radical which consists of carbon atoms and from one to five heteroatoms selected from the group consisting of nitrogen, oxygen and sulfur. For purposes of this invention, the heterocyclyl radical may be a monocyclic, bicyclic or tricyclic ring system, which may include fused or bridged ring systems; and the nitrogen, carbon or sulfur atoms in the heterocyclyl radical may be optionally oxidized; the nitrogen atom may be optionally-quatemized; and the heterocyclyl radical may be aromatic or partially or fully saturated. The heterocyclyl radical may not be attached to the rest of the molecule at any heteroatom atom. Examples of such heterocyclyl radicals include, but are not limited to, azepinyl, acridinyl, benzimidazolyl, benzthiazolyl, benzothiadiazolyl, benzoxazolyl, benzodioxolyl, benzodioxinyl, benzopyranyl, benzopyranonyl, benzofuranyl, benzofuranonyl, benzothienyl (benzothiophenyl), benzotriazolyl, carbazolyl, cinnolinyl, decahydroisoquinolyl, dioxolanyl, furanyl, furanonyl, isothiazolyl, imidazolyl, imidazolinyl, imidazolidinyl, isothiazolidinyl, indolyl, indazolyl, isoindolyl, indolinyl, isoindolinyl, indolizinyl, isoxazolyl, isoxazolidinyl, morpholinyl, naphthyridinyl, oxadiazolyl, octahydroindolyl, octahydroisoindolyl, 2-oxopiperazinyl, 2-oxopiperidinyl, 2-oxopyrrolidinyl, 2-oxoazepinyl, oxazolyl, oxazolidinyl, oxiranyl, piperidinyl, piperazinyl, 4-piperidonyl, phenazinyl, phenothiazinyl, phenoxazinyl, phthalazinyl, pteridinyl, purinyl, pyrrolyl, pyrrolidinyl, pyrazolyl, pyrazolidinyl, pyridinyl, pyrazinyl, pyrimidinyl, pyridazinyl, quinazolinyl, quinoxalinyl, quinolinyl, quinuclidinyl, isoquinolinyl, thiazolyl, thiazolidinyl, thiadiazolyl, triazolyl, tetrazolyl, tetrahydrofuryl, triazinyl, tetrahydropyranyl, thienyl, thiamorpholinyl, thiamorpholinyl sulfoxide, and thiamorpholinyl sulfone. Unless stated otherwise specifically in the specification, the term "heterocyclyl" is meant to include heterocyclyl radicals as defined above which are optionally substituted by one or more substituents selected from the group consisting of alkyl, halo, nitro, cyano, haloalkyl, haloalkoxy, aryl, heterocyclyl, heterocyclylalkyl, —$OR^8$, —$R^7$—$OR^8$, —$C(O)OR^8$, —$R^7$—$C(O)OR^8$, —$C(O)N(R^8)_2$, —$N(R^8)_2$, —$R^7$—$N(R^8)_2$, and —$N(R^8)C(O)R^8$ wherein each $R^7$ is a straight or branched alkylene or alkenylene chain and each $R^8$ is independently hydrogen, alkyl, alkenyl, cycloalkyl, cycloalkylalkyl, aralkyl or aryl.

"Heterocyclylalkyl" refers to a radical of the formula -$R_aR_e$ where $R_a$ is an alkyl radical as defined above and $R_e$ is a heterocyclyl radical as defined above, and if the heterocyclyl is a nitrogen-containing heterocyclyl, the heterocyclyl may be attached to the alkyl radical at the nitrogen atom. The heterocyclyl radical may be optionally substituted as defined above.

In the formulas provided herein, molecular variations are included, which may be based on isosteric replacement. "Isosteric replacement" refers to the concept of modifying chemicals through the replacement of single atoms or entire functional groups with alternatives that have similar size, shape and electro-magnetic properties, e.g. O is the isosteric replacement of S, N, COOH is the isosteric replacement of tetrazole, F is the isosteric replacement of H, sulfonate is the isosteric replacement of phosphate etc.

As used herein, compounds which are "commercially available" may be obtained from standard commercial sources including Acros Organics (Pittsburgh Pa.), Aldrich Chemical (Milwaukee Wiss., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H., Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.), Novabiochem and Argonaut Technology.

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandier et al., "Organic Functional Group Preparations," 2nd Ed., Academic Press, New York, 1983; H. O. House, "Modem Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses. (e.g., those listed above) provide custom synthesis services.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The tTGase inhibitors, or their pharmaceutically acceptable salts may contain one or more asymmetric centers and may thus give rise to enantiomers, diastereomers, and other stereoisomeric forms that may be defined, in terms of absolute stereochemistry, as (R)— or (S)— or, as (D)- or (L)- for amino acids. The present invention is meant to include all such possible isomers, as well as, their racemic and optically pure forms. Optically active (+) and (−), (R)— and (S)—, or (D)- and (L)- isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

The present invention provides the tTGase inhibitors in a variety of formulations for therapeutic administration. In one aspect, the agents are formulated into pharmaceutical compositions by combination with appropriate, pharmaceutically acceptable carriers or diluents, and are formulated into preparations in solid, semi-solid, liquid or gaseous forms, such as tablets, capsules, powders, granules, ointments, solutions, suppositories, injections, inhalants, gels, microspheres, and aerosols. As such, administration of the tTGase inhibitors is achieved in various ways, although oral administration is a preferred route of administration. In some formulations, the tTGase inhibitors are systemic after administration; in others, the inhibitor is localized by virtue of the formulation, such as the use of an implant that acts to retain the active dose at the site of implantation.

In some pharmaceutical dosage forms, the tTGase inhibitors are administered in the form of their pharmaceutically acceptable salts. In some dosage forms, the tTGase inhibitor is used alone, while in others, the tTGase is used in combination with another pharmaceutically active compounds. In the latter embodiment, the other active compound is, in some embodiments, a glutenase that can cleave or otherwise degrade a toxic gluten oligopeptide, as described in the Examples below. The following methods and excipients are merely exemplary and are in no way limiting.

For oral preparations, the agents are used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and in some embodiments, with diluents, buffering agents, moistening agents, preservatives and flavoring agents.

In one embodiment of the invention, the oral formulations comprise enteric coatings, so that the active agent is delivered to the intestinal tract. Enteric formulations are often used to protect an active ingredient from the strongly acid contents of the stomach. Such formulations are created by coating a solid dosage form with a film of a polymer that is insoluble in acid environments and soluble in basic environments. Exemplary films are cellulose acetate phthalate, polyvinyl acetate phthalate, hydroxypropyl methylcellulose phthalate and-hydroxypropyl methylcellulose acetate succinate, methacrylate copolymers and cellulose acetate phthalate.

Other enteric formulations of the tTGase inhibitors of the invention comprise engineered polymer microspheres made of biologically erodable polymers, which display strong adhesive interactions with gastrointestinal mucus and cellular linings, can traverse both the mucosal absorptive epithelium and the follicle-associated epithelium covering the lymphoid tissue of Peyer's patches. The polymers maintain contact with intestinal epithelium for extended periods of time and actually penetrate it, through and between cells. See, for example, Mathiowitz et al. (1997) *Nature* 386 (6623): 410-414. Drug delivery systems can also utilize a core of superporous hydrogels (SPH) and SPH composite (SPHC), as described by Dorkoosh et al. (2001) *J Control Release* 71(3):307-18.

In another embodiment, the tTGase inhibitor or formulation thereof is admixed with food, or used to pre-treat foodstuffs containing glutens.

Formulations are typically provided in a unit dosage form, where the term "unit dosage form," refers to physically discrete units suitable as unitary dosages for human subjects, each unit containing a predetermined quantity of tTGase inhibitor calculated in an amount sufficient to produce the desired effect in association with a pharmaceutically acceptable diluent, carrier or vehicle. The specifications for the unit dosage forms of the present invention depend on the particular complex employed and the effect to be achieved, and the pharmacodynamics associated with each complex in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Depending on the patient and condition being treated and on the administration route, the tTGase inhibitor is administered in dosages of 0.01 mg to 500 mg V/kg body weight per day, e.g. about 20 mg/day for an average person. Dosages are appropriately adjusted for pediatric formulation. Those of skill will readily appreciate that dose levels can vary as a function of the specific inhibitor, the diet of the patient and the gluten content of the diet, the severity of the symptoms, and the susceptibility of the subject to side effects. Some of the inhibitors of the invention are more potent than others. Preferred dosages for a given inhibitor are readily determinable by those of skill in the art by a variety of means. A preferred means is to measure the physiological potency of a given compound.

The methods of the invention are useful in the treatment of individuals suffering from Celiac Sprue and/or dermatitis herpetiformis, by administering an effective dose of a tTGase inhibitor, through a pharmaceutical formulation, and the like. Diagnosis of suitable patients may utilize a variety of criteria known to those of skill in the art. A quantitative increase in antibodies-specific for gliadin, and/or tissue transglutaminase is indicative of the disease. Family histories and the presence of the HLA alleles HLA-DQ2 [DQ(a1*0501, b1*02)] and/or DQ8 [DQ(a1*0301, b1*0302)] are indicative of a susceptibility to the disease. Moreover, as tTG plays an important role in other diseases, such as Huntington's disease and skin diseases in addition to dermatitis herpetiformis, a variety of formulated versions of the compounds of the invention (e.g. topical formulations, intravenous injections) are useful for the treatment of such medical conditions. These conditions include Alzheimer's and Huntington's diseases, where the TGases appear to be a factor in the formation of inappropriate proteinaceous aggregates that may be cytotoxic. In diseases such as progressive supranuclear palsy, Huntington's, Alzheimer's and Parkinson's diseases, the aberrant activation of TGases may be caused by oxidative stress and inflammation.

Therapeutic effect is measured in terms of clinical outcome, or by immunological or biochemical tests. Suppression of the deleterious T-cell activity can be measured by enumeration of reactive Th1 cells, by quantitating the release of cytokines at the sites of lesions, or using other assays for the presence of autoimmune T cells known in the art. Also both the physician and patient can identify a reduction in symptoms of a disease.

Various methods for administration are employed in the practice of the invention. In one preferred embodiment, oral administration, for example with meals, is employed. The dosage of the therapeutic formulation can vary widely, depending upon the nature of the disease, the frequency of administration, the manner of administration, the clearance of the agent from the patient, and the like. The initial dose can be larger, followed by smaller maintenance doses. The dose can be administered as infrequently as weekly or biweekly, or more often fractionated into smaller doses and administered daily, with meals, semi-weekly, and the like, to maintain an effective dosage level.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

EXAMPLE 1

Synthesis of Glutamine Mimetic tTGase Inhibitors

Synthesis of N-(Carbobenzyloxy)-D,L-homocysteine thiolactone (25). To a solution of DL-homocysteine thiolactone hydrochloride (1 eq.) in an aqueous solution of $Na_2CO_3$ (10 eq.) and dioxane (v/v), cooled to 0° C., benzylchloroformate (1 eq) in dioxane is added. After 20 h at room temperature, the bulk of the dioxane is evaporated and the resulting aqueous solution extracted with AcOEt. The combined extracts are washed with brine, dried over sodium sulfate and evaporated. The crude product is triturated in ether and finally filtered. White solid. Yield 95%. $^1$H NMR ($CDCl_3$) δ 1.98 (m, 1H), 2.87 (m, 1H), 3,24-3.34 (m, 2H), 4. 31 (m, 1H), 5.12 (s, 2H), 7.35 (m, 5H)

Synthesis of S-acetyl-N-(carbobenzyloxy)-D,L-homocysteine (26). A solution of N-(Carbobenzyloxy) -D,L-homocysteine thiolactone 25 (1 eq.) in THF:$H_2O$ 1.5:0.5 was degassed three times. A solution of 6M aqueous degassed KOH (3 eq.), was added the thiolactone solution. After the solution was stirred at room temperature for 1.5 h, acetic anhydride (5.3 eq.) was then added dropwise with continued cooling (ice bath), maintaining a temperature of <27 ° C. After an additional 30 min. at room temperature, the reaction was acidified with 6N aqueous HCl to pH 4.3, and then concentrated in vacuo. The concentrate was acidified further with additional 6N aqueous HCl to pH 2.6. The product was extracted with EtOAc. The combined organic extracts were washed three times with saturated brine, dried ($Na_2SO_4$), filtered, and concentrated under vacuum to afford a tacky white solid. The residue was azeotroped three times with toluene to remove residual acetic acid. The solid was collected by filtration using hexane:EtOAc 1:1 and dried to afford racemic 26, free acid form, as a white solid. Yield 85%. TLC $R_f$ 0.48 (EtOAC: AcOH 98:2). $^1$H NMR ($CDCl_3$) δ 1.99 (m, 1H), 2.08 (m, 1H), 2.29 (s, 3H), 2.86-2.98 (m, 2H), 4.14 (m, 1H), 5.12 (s, 2H), 7.35 (m, 5H).

Synthesis of (31). To a solution of the free racemic acid of S-acetyl-N-(carbobenzyloxy) -D,L-homocysteine 26 (1 eq.) in DCM at 0° C. was added 1-hydroxybenzotrizole hydrate (HOBt, 1.1 eq.), followed by 1-[3-(dimethylamino)propyl]-3-ethylcarbodiimide hydrochloride (EDPI, 1 eq.). The resulting suspension was stirred at 0° C. for 30 min and then a solution of glycine benzylester 30 (1 eq.) in DCM was added, followed by dropwise addition of a solution of 4-dimethylaminopyridine (DMAP, 1.2 eq.) in DCM. The resulting suspension was stirred at room temperature for 20 h. The reaction mixture was partitioned between EtOAc and 5% aqueous $NaHPO_4$. The separated organic layer was then washed with 5% aqueous $NaHPO_4$, satured aqueous $Na_2CO_3$, $H_2O$, and brine, dried over $Na_2SO_4$, and filtered. Yhe filtrate was concentrated in vacuo, and the residu was flash chromatographed on a short silica gel column to afford the pure dipeptide 31 as a colorless oil. Yield 75%. $^1$H NMR ($CDCl_3$) δ1.98 (m, 1H), 2.05-2.13 (m, 3H), 2.29 (s, 3H), 2.86 (m, 1H), 2.98 (m, 1H), 4.14 (m, 1H), 5.10-5.14 (m, 4H), 7.28-7.42 (m, 10H).

Synthesis of (32). A solution of 31 (1 eq.) and NaOAc (10 eq.) in HOAc:$H_2O$ 5:1 was stirred below 10° C. Gaseous chlorine was bubbled into the solution. After 10 min argon was blown through the yellow mixture for 10 min to remove excess $Cl_2$ and the solvent was evaporated. The residue was partitioned between EtOAc and $H_2O$. The EtOAc solution was washed with brine, dried, and evaporated to the yellow oily sulfonylchloride. This product was used without further purification in the next stage. A solution of the crude sulfonylchloride (1 eq.) in $CHCl_3$ was stirred below 10° C. Gaseous ammoniac was bubbled into the solution. After 20 min, the mixture was stirred for 30 min, allowed to warm to room temperature, and evaporated to dryness. The residue was partitioned between EtOAc and $H_2O$. The EtOAc solution was washed with brine, dried, and evaporated to a colorless oil. Yield 75%. $^1$H NMR ($CDCl_3$) δ2.01 (m, 1H), 2.13 (s, 2H), 2.22-2.32 (m, 1H), 3.21-3.31 (m, 2H), 4.14 (m, 1H), 5.10-5.14 (m, 4H), 7.27-7.41 (m,$_{10}$H).

Synthesis of (33). The benzyl ester 32 (1 eq.) was stirred for 2 h in a mixture of aqueous 1N NaOH:EtOH 1.2:3 (10 eq.). The reaction mixture was evaporated to dryness and the residue was dissolved in a small amount of $H_2O$. The solution was filtered into a centrifuge tube and acidified to pH 3. The gelatinous precipitate was isolated by centrifugation, washed with $CHCl_3$, and dried to a white solid. Yield 60%. MS m/z 372.3 [M-H$^-$]$^-$.

Synthesis of Fmoc-Acivicin 45. 3.1 ml of a 0.75 M solution of Fmoc-N-hydroxysuccinimide in acetone was added to 0.4 g acivicin (2.25 mmol, Biomol) dissolved in 3.1 ml of a 10% $Na_2CO_3$ aqueous solution. The slurry was stirring for 4 hours and the pH of was maintained at 9.0 by addition of $Na_2CO_3$. The solvent was removed by rotary evaporation, the residual solid was dissolved in 0.6 M HCL, extracted with ethyl acetate and concentrated to a yellow oil. Recrystallization from ethyl acetate: hexane yielded 0.62 9 (1.55 mmol, 70%) of the desired product as white crystals. $R_f$ ($CH_2Cl_2$: iPrOH: AcOH=100:3:1)=0.3

¹H (d⁶-acetone, 200 MHz) cpm=7.87 ArH (2H, d, J=7.4 Hz); 7.73 ArH (2H, d, J=7 Hz); 7.28-7.48 ArH (4H, m); 7.17 NH (1H, d, J=8 Hz); 5.22 CH₂CHO (1H, m); 4.66 (1H, q, J=4.4 Hz); 4.2-4.4 (3H); 3.6-3.4 (2H). m [M-Na]⁺=423.4, 425.3 g/mol.

Synthesis of Pro-Gln-Pro-Aci-Leu-Pro-Tyr 46. PQPAciLPY was synthesized by standard Fmoc solid phase chemistry using Fmoc-acivicin and commercially available building blocks in a 25 µmol scale. Preparative reversed phase HPLC purification yielded 4 OD$_{275}$ (3.4 µmol, 14%). LC-MS: R$_f$=12 min, [M+H]⁺=874.6.

Synthesis of Ac-Pro-Gln-Pro-Don-Leu-Pro-Phe-NH₂ 41.72 mg (8.3 µmol) of HPLC-purified, lyophilized Ac-Pro-Gln-Pro-Glu-Leu-Pro-Phe-NH₂ in 1 ml THF and 15 µl (135 µmol) N-methyl morpholine were mixed with 13 µl (100 µmol) at 0° C., followed by addition of up to 0.5 mol of a saturated diazomethane solution in dry ether generated from Diazald as described by the supplier. After 1 hour the solvents were evaporated, the residual solid was extracted with ethyl ester and a 5% aqueous solution of NH₄HCO₃, and the combined aqueous phases were concentrated by rotary evaporation. The crude product was purified by preparative reversed phase HPLC on a Beckman Ultrashpere C18 column (15× 2.54 cm) using a 1% NH₄HCO₃ as buffer A and 0.5% NH₄HCO₃, 80% acetonitrile as buffer B. The product eluting at 22.5% buffer B was concentrated yielding 16 mg (150 OD$_{275}$) of lyophyllized product. [M+Na]⁺=914.4.

Synthesis of (S)-2-Benzyloxycarbonylamino-4-sulfamoyl-butyric acid ethyl ester (a) (Cbz-homocys)₂

1.00 g (3.65 mmol) of L-homocystine (Bachem, Calif.) was dissolved in 15 ml of 1:1 (v/v) mixture of 1,4-dioxane and water, and NaOH (0.30 g, 2.0 eq) was added. To the solution cooled down to 0° C., benzyl chloroformate (1.27 ml, 2.3 eq) was added dropwise as the pH of the solution was maintained slightly basic by simultaneous addition of 1 N NaOH. After stirring for 1 hr, the solution was washed with ether, acidified with 6 N HCl and extracted with ethyl acetate. The organic layer was washed with brine and dried over Na₂SO₄. After filtration, the solvent was removed by evaporation and the residue was dried under vacuum to give the title compound as a white solid (1.83 g, 92%).

¹H NMR (DMSO-d₆, 200 MHz): δ=7.59(d, 2H, J=8.0 Hz), 7.29-7.26(m, 10H), 4.96(s, 4H), 4.03-3.97(m, 2H), 2.70-2.62 (m, 4H), 2.05-1.84(m, 4H) MS (ESI): m/z=536.9 [M+H]⁺, 559.1 [M+Na]⁺ (b) (Cbz-homocys-OEt)₂

1.00 g (1.86 mmol) of (Cbz-homocys)₂ was dissolved in 10 ml EtOH. To the solution cooled down to 0° C., SOCl₂ (0.33 ml, 2.4 eq) was added dropwise and the stirring was continued overnight at room temperature. The solvent was removed by evaporation and the residue was redissolved in ethyl acetate. The solution was washed with sat. NaHCO₃ solution and brine, and dried over Na₂SO₄. After filtration, the solvent was removed by evaporation and the residue was dried under vacuum to give the title compound as a white solid (1.10 g, quant.).

¹H NMR (CDCl₃, 200 MHz): δ=7.30-7.27(m, 10H), 5.40 (d, 2H, J=8.2 Hz), 5.04(s, 4H), 4.43-4.38(m, 2H), 4.15(q, 4H, J=7.0 Hz), 2.69-2.61(m, 4H), 2.20-1.94(m, 4H), 1.22(t, 3H, J=7.0 Hz) MS (ESl): m/z=592.9 [M+H]⁺, 615.2 [M+Na]⁺ (c) (S)-2-Benzyloxycarbonylamino-4-sulfamoyl-butyric acid ethyl ester 1.00 g (1.77 mmol) of (Cbz-homocys-OEt)₂ was dissolved in 12 ml of 2:1 mixture of CCl₄ and EtOH. Cl₂ (g) was bubbled through the solution cooled down to 0° C. for 1 hr. Stirring was continued for 20 min at room temperature with Ar bubbling. The solvents were removed by evaporation and the residue was dried under vacuum.

This (S)-2-benzyloxycarbonylamino4-chlorosulfonyl-butyric acid ethyl ester was dissolved in 10 ml CH₂Cl₂ and NH₃ (g) was bubbled through the solution at 0° C. for 30 min. The solvent was removed by evaporation and the residue was redissolved in ethyl acetate. The solution was washed with brine and dried over Na₂SO₄. After filtration, the solvent was removed by evaporation and the residue was purified by SiO₂ chromatography to give the title compound as a white solid (0.95 g, 82%).

¹H NMR (CDCl₃, 200 MHz): δ=7.32-7.30(m, 5H), 5.49(d, 1H, J=8.4 Hz), 5.07(s, 2H), 4.71 (br, 2H), 4.50-4.45(m, 1H), 4.18(q, 2H, J=7.2 Hz), 3.21-3.13(m, 2H), 2.42-2.14(m, 2H), 1.24(t, 3H, J=7.2 Hz) MS (ESI): m/z=367.1 [M+Na]⁺

Synthesis of (S)-2-Benzyloxycarbonylamino-4-hydrazinosulfonyl-butyrc acid ethyl ester (S)-2-benzyloxycarbonylamino-4-chlorosulfonyl-butyric acid ethyl ester, prepared from 0.10 g of (Cbz-homocys-OEt)₂ as above, was reacted with hydrazine monohydrate (38 µl, 2.2 eq) in 2 ml CH₂Cl₂ for 1 hr. The solution was diluted with ethyl acetate and washed with 0.1 N HCl, sat. NaHCO₃ solution and brine. The solvents were evaporated and the residue was purified to by SiO₂ chromatography to give the title compound as clear oil (84 mg, 70%).

¹H NMR (CDCl₃, 200 MHz): δ=7.30-7.28(m, 5H), 5.54(d, 1H, J=8.4 Hz), 5.05(s, 2H), 4.45-4.40(m, 1H), 4.16(q, 2H, J=7.0 Hz), 4.11(br, 3H), 3.24-3.08(m, 2H), 2.38-2.02(m, 2H), 1.22(t, 3H, J=7.0 Hz) MS (ESl): m/z=352.1 [M+Na]⁺

Synthesis of (S)-2-Benzyloxycarbonylamino-4-phenylhydrazinosulfonyl-butyric acid ethyl ester. According to the procedure described for the synthesis of (S)-2-Benzyloxycarbonylamino-4-hydrazinosulfonyl-butyric acid ethyl ester, the title compound was obtained from phenylhydrazine as slightly orange oil.

¹H NMR (CDCl₃, 200 MHz): δ=7.29-7.15(m, 9H), 6.87(d, 2H, J=7.0 Hz), 6.09(s,1H), 5.31 (d, 1H, J=7.8 Hz), 5.02(s, 2H), 4.34-4.30(m, 1H), 4.10(q, 2H, J=7.2 Hz), 3.07-2.99(m, 2H), 2.36-2.04(m, 2H), 1.18(t, 3H, J=7.2 Hz) MS (ESI): m/z=458.0 [M+Na]⁺

Inhibition of tTG. tTG (9 µM) was inactivated in 200 mM MOPS, pH=7.1, 5 mM CaCl₂, 1 mM ETDA at 30° C. containing 0-600 µM Pro-Gln-Pro-Aci-Leu-Pro-Tyr [SEQ ID NO:36]. Every 20 minutes a 40 µul aliquot was removed and residual tTG activity was assayed in 0.5 ml reaction containing 200 mM MOPS, pH=7.1, 5 mM CaCl₂, 1 mM ETDA, 10 mM α-ketoglutarate, 180 U/ml glutamate dehydrogenase (Biozyme laboratories) at 30° C. for 20 minutes by measuring the decrease of absorption at 340 nm. Residual activity was corrected by the corresponding uninhibited tTG reaction (0 µM inhibitor) and fitted to an exponential decay. Kinetic parameters were obtained by double-reciprocal plotting of the apparent second-order inactivation constant or, for sulfonamides and sulfonyl hydrazides, by fitting the data for reversible inhibitors to a standard Michaelis Menten equation with a competitive inhibition constant. The results of these inhibition experiments are shown in Tables 1, and 2 and 3 below.

TABLE 1

Kinetic parameters of catalysis and inhibition of tissue transglutaminase by reactive glutamine peptide analogs. The reactive glutamine (—X—) in the peptide substrate was substituted by the inhibitory residue acivicin (Aci) or 6-diazo-5-oxo-norleucine (DON).

| Reactive Motif: Scaffold: | Gln | | | Aci | | | DON | | |
|---|---|---|---|---|---|---|---|---|---|
| | $k_{cat}$ [min$^{-1}$] | $K_M$ [M] | $k_{cat}/K_M$ [min$^{-1}$M$^{-1}$] | $k_{inh}$ [min$^{-1}$] | $K_I$ [M] | $k_{inh}/K_I$ [min$^{-1}$M$^{-1}$] | $k_{inh}$ [min$^{-1}$] | $K_I$ [M] | $k_{inh}/K_I$ [min$^{-1}$M$^{-1}$] |
| H—X—OH | — | >0.2 | ≤2 | 0.015 | 0.087 | 0.17 | 0.025 | 0.13 | 0.2 |
| Cbz-X—OMe | — | >0.03 | 90 | — | — | — | 0.12 | $1.35 \times 10^{-4}$ | 890 |
| PQP-X-LPY [SEQ ID NO:33] | 28 | $3 \times 10^{-4}$ | $8.2 \times 10^{-4}$ | 0.014 | $7.8 \times 10^{-4}$ | 18 | — | — | — |
| Ac-PQP-X-LPF-NH$_2$ [SEQ ID NO:32] | 40 | $4 \times 10^{-4}$ | $9.7 \times 10^4$ | — | — | — | 0.2 | $7 \times 10^{-8}$ | $2.9 \times 10^6$ |

TABLE 2

Kinetic parameters of catalysis and inhibition of tissue transglutaminase by Sab and Z-Sab-Gly.

| Compound | Sab | Z-Sab-Gly |
|---|---|---|
| $K_I$ [mM] | >200 | 8 |
| $k_{inh}$ [min$^{-1}$] | — | — |
| $k_{inh}/K_I$ [mM$^{-1}$min$^{-1}$] | — | — |

TABLE 3

Tissue transglutaminase inhibition by sulfonamides and sulfonyl hydrazides

| tested compound | inhibition constant (M) |
|---|---|
| (S)-2-Benzyloxycarbonylamino-4-sulfamoyl-butyric acid ethyl ester | $4.4 \times 10^{-3}$ |
| (S)-2-Benzyloxycarbonylamino-4-hydrazinosulfonyl-butyric acid ethyl ester | $2.2 \times 10^{-3}$ |
| (S)-2-Benzyloxycarbonylamino-4-phenyl-hydrazinosulfonyl-butyric acid ethyl ester | $1.3 \times 10^{-4}$ |

The above results demonstrate that the compounds tested have tTGase inhibitory activity.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Moreover, due to biological functional equivalency considerations, changes can be made in protein structure without affecting the biological action in kind or amount. All such modifications are intended to be included within the scope of the appended claims.

What is claimed is:

1. A method of treating Celiac Sprue, the method comprising:

administering to a patient an effective dose of a tTGase inhibitor having the formula

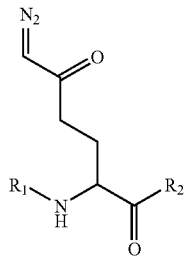

wherein $R_1$ is selected from the group consisting of PQP, Ac-PQP, PQPQLPYPQP (SEQ ID NO:21), Ac-PQPQLPFPQP (SEQ ID NO:22), QLQPFPQP (SEQ ID NO:23), LQLQPFPQPLPYPQP (SEQ ID NO:24); and $R_2$ is selected from the group consisting of LPY, LPF-NH$_2$, LPYPQPQLPY (SEQ ID NO:25), LPFPQPQLPF-NH$_2$ (SEQ ID NO:26), LPYPQPQLP (SEQ ID NO:27), and LPYPQPQLPYPQPQPF (SEQ ID NQ:28)

wherein said tTGase inhibitor attenuates gluten toxicity in said patient.

2. The method of claim 1, wherein the tTGase inhibitor is:

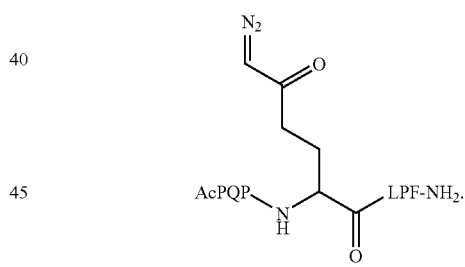

3. The method of claim 1, wherein said tTGase inhibitor is administered with a glutenase.

4. The method according to claim 1, wherein said tTGase inhibitor is administered orally.

5. The method according to claim 1, wherein said tTGase inhibitor is contained in a formulation that comprises an enteric coating.

* * * * *

UNITED STATES PATENT AND TRADEMARK OFFICE
CERTIFICATE OF CORRECTION

| | |
|---|---|
| PATENT NO. | : 7,605,150 B2 |
| APPLICATION NO. | : 10/514177 |
| DATED | : October 20, 2009 |
| INVENTOR(S) | : Khosla et al. |

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 573 days.

Delete the phrase "by 573 days" and insert -- by 1105 days --

Signed and Sealed this

Twentieth Day of April, 2010

David J. Kappos
*Director of the United States Patent and Trademark Office*

SEQUENCE LISTING

```
<160> NUMBER OF SEQ ID NOS: 39

<210> SEQ ID NO 1
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 1

Pro Gln Pro Gln Leu Pro Tyr
 1               5

<210> SEQ ID NO 2
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 2
```

```
Pro Gln Pro Glu Leu Pro Tyr
  1               5

<210> SEQ ID NO 3
<211> LENGTH: 33
<212> TYPE: PRT
<213> ORGANISM: Artificial Sequence
<220> FEATURE:
<223> OTHER INFORMATION: synthetic polypeptide

<400> SEQUENCE: 3

Leu Gln Leu Gln Pro Phe Pro Gln Pro Gln Leu Pro Tyr Pro Gln Pro
  1               5                  10                  15

Gln Leu Pro Tyr Pro Gln Pro Gln Leu Pro Tyr Pro Gln Pro Gln Pro
             20                  25                  30

Phe

<210> SEQ ID NO 4
<211> LENGTH: 13
<212> TYPE: PRT
<213> ORGANISM: Artificial Sequence
<220> FEATURE:
<223> OTHER INFORMATION: synthetic polypeptide

<400> SEQUENCE: 4

Pro Gln Pro Gln Leu Pro Tyr Pro Gln Pro Gln Leu Pro
  1               5                  10

<210> SEQ ID NO 5
<211> LENGTH: 46
<212> TYPE: PRT
<213> ORGANISM: Artificial Sequence
<220> FEATURE:
<223> OTHER INFORMATION: synthetic polypeptide

<400> SEQUENCE: 5

Pro Gln Pro Gln Leu Pro Tyr Pro Gln Pro Gln Leu Pro Leu Gln Leu
  1               5                  10                  15

Gln Pro Phe Pro Gln Pro Gln Leu Pro Tyr Pro Gln Pro Gln Leu Pro
             20                  25                  30

Tyr Pro Gln Pro Gln Leu Pro Tyr Pro Gln Pro Gln Pro Phe
             35                  40                  45

<210> SEQ ID NO 6
<211> LENGTH: 34
<212> TYPE: PRT
<213> ORGANISM: Artificial Sequence
<220> FEATURE:
<223> OTHER INFORMATION: synthetic polypeptide

<400> SEQUENCE: 6

Gln Pro Gln Pro Phe Pro Pro Gln Leu Pro Tyr Pro Gln Thr Gln Pro
  1               5                  10                  15

Phe Pro Pro Gln Gln Pro Tyr Pro Gln Pro Gln Pro Gln Tyr Pro Gln
             20                  25                  30

Pro Gln

<210> SEQ ID NO 7
<211> LENGTH: 35
<212> TYPE: PRT
<213> ORGANISM: Artificial Sequence
<220> FEATURE:
<223> OTHER INFORMATION: synthetic polypeptide
```

<400> SEQUENCE: 7

Gln Gln Gln Pro Phe Pro Gln Pro Ile Pro Gln Pro Gln Pro
1               5                   10                  15

Tyr Pro Gln Gln Pro Gln Pro Tyr Pro Gln Gln Pro Phe Pro Pro Gln
            20                  25                  30

Gln Pro Phe
        35

<210> SEQ ID NO 8
<211> LENGTH: 30
<212> TYPE: PRT
<213> ORGANISM: Artificial Sequence
<220> FEATURE:
<223> OTHER INFORMATION: synthetic polypeptide

<400> SEQUENCE: 8

Gln Pro Phe Pro Gln Pro Gln Gln Thr Phe Pro Gln Gln Pro Gln Leu
1               5                   10                  15

Pro Phe Pro Gln Gln Pro Gln Gln Pro Phe Pro Gln Pro Gln
            20                  25                  30

<210> SEQ ID NO 9
<211> LENGTH: 16
<212> TYPE: PRT
<213> ORGANISM: Artificial Sequence
<220> FEATURE:
<223> OTHER INFORMATION: synthetic polypeptide

<400> SEQUENCE: 9

Val Gln Trp Pro Gln Gln Gln Pro Val Pro Gln Pro His Gln Pro Phe
1               5                   10                  15

<210> SEQ ID NO 10
<211> LENGTH: 14
<212> TYPE: PRT
<213> ORGANISM: Artificial Sequence
<220> FEATURE:
<223> OTHER INFORMATION: synthetic polypeptide

<400> SEQUENCE: 10

Val Gln Gly Gln Gly Ile Ile Gln Pro Gln Gln Pro Ala Gln
1               5                   10

<210> SEQ ID NO 11
<211> LENGTH: 26
<212> TYPE: PRT
<213> ORGANISM: Artificial Sequence
<220> FEATURE:
<223> OTHER INFORMATION: synthetic polypeptide

<400> SEQUENCE: 11

Phe Leu Gln Pro Gln Gln Pro Phe Pro Gln Gln Pro Gln Gln Pro Tyr
1               5                   10                  15

Pro Gln Gln Pro Gln Gln Pro Phe Pro Gln
            20                  25

<210> SEQ ID NO 12
<211> LENGTH: 24
<212> TYPE: PRT
<213> ORGANISM: Artificial Sequence
<220> FEATURE:
<223> OTHER INFORMATION: synthetic polypeptide

<400> SEQUENCE: 12

```
Phe Ser Gln Pro Gln Gln Gln Phe Pro Gln Pro Gln Gln Pro Gln Gln
1               5                   10                  15

Ser Phe Pro Gln Gln Gln Pro Pro
            20
```

<210> SEQ ID NO 13
<211> LENGTH: 30
<212> TYPE: PRT
<213> ORGANISM: Artificial Sequence
<220> FEATURE:
<223> OTHER INFORMATION: synthetic polypeptide

<400> SEQUENCE: 13

```
Gln Pro Phe Pro Gln Pro Gln Gln Pro Thr Pro Ile Gln Pro Gln Gln
1               5                   10                  15

Pro Phe Pro Gln Arg Pro Gln Gln Pro Phe Pro Gln Pro Gln
            20                  25                  30
```

<210> SEQ ID NO 14
<211> LENGTH: 13
<212> TYPE: PRT
<213> ORGANISM: Artificial Sequence
<220> FEATURE:
<223> OTHER INFORMATION: synthetic polypeptide

<400> SEQUENCE: 14

```
Val Gln Gly Gln Gly Ile Ile Gln Pro Gln Gln Pro Ala
1               5                   10
```

<210> SEQ ID NO 15
<211> LENGTH: 7
<212> TYPE: PRT
<213> ORGANISM: Artificial Sequence
<220> FEATURE:
<223> OTHER INFORMATION: synthetic polypeptide
<220> FEATURE:
<221> NAME/KEY: VARIANT
<222> LOCATION: (4)...(4)
<223> OTHER INFORMATION: Xaa = glutamines identified as "(Q->E)", E
      being the amino acid formed by deamidation of glutamine
<220> FEATURE:
<221> NAME/KEY: VARIANT
<222> LOCATION: 4
<223> OTHER INFORMATION: Xaa = Any Amino Acid

<400> SEQUENCE: 15

```
Pro Gln Pro Xaa Leu Pro Tyr
1               5
```

<210> SEQ ID NO 16
<211> LENGTH: 13
<212> TYPE: PRT
<213> ORGANISM: Artificial Sequence
<220> FEATURE:
<223> OTHER INFORMATION: synthetic polypeptide
<220> FEATURE:
<221> NAME/KEY: VARIANT
<222> LOCATION: (4)...(4)
<223> OTHER INFORMATION: Xaa = glutamines identified as "(Q->E)", E
      being the amino acid formed by deamidation of glutamine
<220> FEATURE:
<221> NAME/KEY: VARIANT
<222> LOCATION: 4
<223> OTHER INFORMATION: Xaa = Any Amino Acid

<400> SEQUENCE: 16

```
Pro Gln Pro Xaa Leu Pro Tyr Pro Gln Pro Gln Leu Pro
1               5                   10
```

```
<210> SEQ ID NO 17
<211> LENGTH: 33
<212> TYPE: PRT
<213> ORGANISM: Artificial Sequence
<220> FEATURE:
<223> OTHER INFORMATION: synthetic polypeptide
<220> FEATURE:
<221> NAME/KEY: VARIANT
<222> LOCATION: (10)...(10)
<223> OTHER INFORMATION: Xaa = glutamines identified as "(Q->E)", E
      being the amino acid formed by deamidation of glutamine
<220> FEATURE:
<221> NAME/KEY: VARIANT
<222> LOCATION: (24)...(24)
<223> OTHER INFORMATION: Xaa = glutamines identified as "(Q->E)", E
      being the amino acid formed by deamidation of glutamine
<220> FEATURE:
<221> NAME/KEY: VARIANT
<222> LOCATION: 10, 24
<223> OTHER INFORMATION: Xaa = Any Amino Acid

<400> SEQUENCE: 17

Leu Gln Leu Gln Pro Phe Pro Gln Pro Xaa Leu Pro Tyr Pro Gln Pro
 1               5                  10                  15

Gln Leu Pro Tyr Pro Gln Pro Xaa Leu Pro Tyr Pro Gln Pro Gln Pro
            20                  25                  30

Phe

<210> SEQ ID NO 18
<211> LENGTH: 24
<212> TYPE: PRT
<213> ORGANISM: Artificial Sequence
<220> FEATURE:
<223> OTHER INFORMATION: synthetic polypeptide
<220> FEATURE:
<221> NAME/KEY: VARIANT
<222> LOCATION: (5)...(5)
<223> OTHER INFORMATION: Xaa = glutamines identified as "(Q->E)", E
      being the amino acid formed by deamidation of glutamine
<220> FEATURE:
<221> NAME/KEY: VARIANT
<222> LOCATION: (7)...(7)
<223> OTHER INFORMATION: Xaa = glutamines identified as "(Q->E)", E
      being the amino acid formed by deamidation of glutamine
<220> FEATURE:
<221> NAME/KEY: VARIANT
<222> LOCATION: (20)...(20)
<223> OTHER INFORMATION: Xaa = glutamines identified as "(Q->E)", E
      being the amino acid formed by deamidation of glutamine
<220> FEATURE:
<221> NAME/KEY: VARIANT
<222> LOCATION: (22)...(22)
<223> OTHER INFORMATION: Xaa = glutamines identified as "(Q->E)", E
      being the amino acid formed by deamidation of glutamine
<220> FEATURE:
<221> NAME/KEY: VARIANT
<222> LOCATION: 5, 7, 20, 22
<223> OTHER INFORMATION: Xaa = Any Amino Acid

<400> SEQUENCE: 18

Phe Ser Gln Pro Xaa Gln Xaa Phe Pro Gln Pro Gln Gln Pro Gln Gln
 1               5                  10                  15

Ser Phe Pro Xaa Gln Xaa Pro Pro
            20

<210> SEQ ID NO 19
<211> LENGTH: 14
<212> TYPE: PRT
<213> ORGANISM: Artificial Sequence
<220> FEATURE:
```

```
<223> OTHER INFORMATION: synthetic polypeptide
<220> FEATURE:
<221> NAME/KEY: VARIANT
<222> LOCATION: (10)...(10)
<223> OTHER INFORMATION: Xaa = glutamines identified as "(Q->E)", E
      being the amino acid formed by deamidation of glutamine
<220> FEATURE:
<221> NAME/KEY: VARIANT
<222> LOCATION: 10
<223> OTHER INFORMATION: Xaa = Any Amino Acid

<400> SEQUENCE: 19

Val Gln Gly Gln Gly Ile Ile Gln Pro Xaa Gln Pro Ala Gln
1               5                   10

<210> SEQ ID NO 20
<211> LENGTH: 26
<212> TYPE: PRT
<213> ORGANISM: Artificial Sequence
<220> FEATURE:
<223> OTHER INFORMATION: synthetic polypeptide
<220> FEATURE:
<221> NAME/KEY: VARIANT
<222> LOCATION: (10)...(10)
<223> OTHER INFORMATION: Xaa = glutamines identified as "(Q->E)", E
      being the amino acid formed by deamidation of glutamine
<220> FEATURE:
<221> NAME/KEY: VARIANT
<222> LOCATION: (13)...(13)
<223> OTHER INFORMATION: Xaa = glutamines identified as "(Q->E)", E
      being the amino acid formed by deamidation of glutamine
<220> FEATURE:
<221> NAME/KEY: VARIANT
<222> LOCATION: 10, 13
<223> OTHER INFORMATION: Xaa = Any Amino Acid

<400> SEQUENCE: 20

Phe Leu Gln Pro Gln Gln Pro Phe Pro Xaa Gln Pro Xaa Gln Pro Tyr
1               5                   10                  15

Pro Gln Gln Pro Gln Gln Pro Phe Pro Gln
            20                  25

<210> SEQ ID NO 21
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 21

Pro Gln Pro Gln Leu Pro Tyr Pro Gln Pro
1               5                   10

<210> SEQ ID NO 22
<211> LENGTH: 10
<212> TYPE: PRT
<213> ORGANISM: Artificial Sequence
<220> FEATURE:
<223> OTHER INFORMATION: synthetic polypeptide
<220> FEATURE:
<221> NAME/KEY: ACETYLATION
<222> LOCATION: (1)...(1)

<400> SEQUENCE: 22

Pro Gln Pro Gln Leu Pro Phe Pro Gln Pro
1               5                   10

<210> SEQ ID NO 23
<211> LENGTH: 8
<212> TYPE: PRT
```

```
<213> ORGANISM: Artificial Sequence
<220> FEATURE:
<223> OTHER INFORMATION: synthetic polypeptide

<400> SEQUENCE: 23

Gln Leu Gln Pro Phe Pro Gln Pro
1               5

<210> SEQ ID NO 24
<211> LENGTH: 15
<212> TYPE: PRT
<213> ORGANISM: Artificial Sequence
<220> FEATURE:
<223> OTHER INFORMATION: synthetic polypeptide

<400> SEQUENCE: 24

Leu Gln Leu Gln Pro Phe Pro Gln Pro Leu Pro Tyr Pro Gln Pro
1               5                   10                  15

<210> SEQ ID NO 25
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 25

Leu Pro Tyr Pro Gln Pro Gln Leu Pro Tyr
1               5                   10

<210> SEQ ID NO 26
<211> LENGTH: 10
<212> TYPE: PRT
<213> ORGANISM: Artificial Sequence
<220> FEATURE:
<223> OTHER INFORMATION: synthetic polypeptide
<220> FEATURE:
<221> NAME/KEY: VARIANT
<222> LOCATION: (10)...(10)
<223> OTHER INFORMATION: phenylalanine with  NH2 attached

<400> SEQUENCE: 26

Leu Pro Phe Pro Gln Pro Gln Leu Pro Phe
1               5                   10

<210> SEQ ID NO 27
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 27

Leu Pro Tyr Pro Gln Pro Gln Leu Pro
1               5

<210> SEQ ID NO 28
<211> LENGTH: 16
<212> TYPE: PRT
<213> ORGANISM: Artificial Sequence
<220> FEATURE:
<223> OTHER INFORMATION: synthetic polypeptide

<400> SEQUENCE: 28

Leu Pro Tyr Pro Gln Pro Gln Leu Pro Tyr Pro Gln Pro Gln Pro Phe
1               5                   10                  15
```

<210> SEQ ID NO 29
<211> LENGTH: 7
<212> TYPE: PRT
<213> ORGANISM: Artificial Sequence
<220> FEATURE:
<223> OTHER INFORMATION: synthetic polypeptide
<220> FEATURE:
<221> NAME/KEY: ACETYLATION
<222> LOCATION: (1)...(1)
<220> FEATURE:
<221> NAME/KEY: VARIANT
<222> LOCATION: (7)...(7)
<223> OTHER INFORMATION: phenylalanine with a NH2 attached

<400> SEQUENCE: 29

Pro Gln Pro Gln Leu Pro Phe
1               5

<210> SEQ ID NO 30
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 30

Gln Pro Phe Pro Gln Pro
1               5

<210> SEQ ID NO 31
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 31

Leu Pro Tyr Pro Gln Pro Gln
1               5

<210> SEQ ID NO 32
<211> LENGTH: 7
<212> TYPE: PRT
<213> ORGANISM: Artificial Sequence
<220> FEATURE:
<223> OTHER INFORMATION: synthetic polypeptide
<220> FEATURE:
<221> NAME/KEY: ACETYLATION
<222> LOCATION: (1)...(1)
<220> FEATURE:
<221> NAME/KEY: VARIANT
<222> LOCATION: (7)...(7)
<223> OTHER INFORMATION: phenylalanine with a NH2 attached
<220> FEATURE:
<221> NAME/KEY: VARIANT
<222> LOCATION: 4
<223> OTHER INFORMATION: Xaa = Any Amino Acid

<400> SEQUENCE: 32

Pro Gln Pro Xaa Leu Pro Phe
1               5

<210> SEQ ID NO 33
<211> LENGTH: 7
<212> TYPE: PRT
<213> ORGANISM: Artificial Sequence
<220> FEATURE:
<223> OTHER INFORMATION: synthetic polypeptide
<220> FEATURE:
<221> NAME/KEY: VARIANT
<222> LOCATION: 4

```
<223> OTHER INFORMATION: Xaa = Any Amino Acid

<400> SEQUENCE: 33

Pro Gln Pro Xaa Leu Pro Tyr
 1               5

<210> SEQ ID NO 34
<211> LENGTH: 7
<212> TYPE: PRT
<213> ORGANISM: Artificial Sequence
<220> FEATURE:
<223> OTHER INFORMATION: synthetic polypeptide
<220> FEATURE:
<221> NAME/KEY: ACETYLATION
<222> LOCATION: (1)...(1)
<220> FEATURE:
<221> NAME/KEY: VARIANT
<222> LOCATION: (7)...(7)
<223> OTHER INFORMATION: phenylalanine with a NH2 attached

<400> SEQUENCE: 34

Pro Gln Pro Glu Leu Pro Phe
 1               5

<210> SEQ ID NO 35
<211> LENGTH: 7
<212> TYPE: PRT
<213> ORGANISM: Artificial Sequence
<220> FEATURE:
<223> OTHER INFORMATION: synthetic polypeptide
<220> FEATURE:
<221> NAME/KEY: VARIANT
<222> LOCATION: 4
<223> OTHER INFORMATION: Xaa = Any Amino Acid

<400> SEQUENCE: 35

Pro Gln Pro Xaa Leu Pro Tyr
 1               5

<210> SEQ ID NO 36
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 36

Pro Gln Pro Ala Leu Pro Tyr
 1               5

<210> SEQ ID NO 37
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 37

Pro Gln Pro Ala Leu Pro Tyr
 1               5

<210> SEQ ID NO 38
<211> LENGTH: 7
<212> TYPE: PRT
<213> ORGANISM: Artificial Sequence
<220> FEATURE:
<223> OTHER INFORMATION: synthetic polypeptide
<220> FEATURE:
<221> NAME/KEY: ACETYLATION
```

```
-continued

<222> LOCATION: (1)...(1)
<220> FEATURE:
<221> NAME/KEY: VARIANT
<222> LOCATION: (4)...(4)
<223> OTHER INFORMATION: Xaa = Don
<220> FEATURE:
<221> NAME/KEY: VARIANT
<222> LOCATION: (7)...(7)
<223> OTHER INFORMATION: Phenylalanine with a NH2 attached

<400> SEQUENCE: 38

Pro Gln Pro Xaa Leu Pro Phe
 1               5

<210> SEQ ID NO 39
<211> LENGTH: 7
<212> TYPE: PRT
<213> ORGANISM: Artificial Sequence
<220> FEATURE:
<223> OTHER INFORMATION: synthetic polypeptide
<220> FEATURE:
<221> NAME/KEY: ACETYLATION
<222> LOCATION: (1)...(1)
<220> FEATURE:
<221> NAME/KEY: VARIANT
<222> LOCATION: (7)...(7)
<223> OTHER INFORMATION: Phenylalanine with a NH2 attached

<400> SEQUENCE: 39

Pro Gln Pro Glu Leu Pro Phe
 1               5
```